(12) United States Patent
Chew et al.

(10) Patent No.: US 7,294,146 B2
(45) Date of Patent: Nov. 13, 2007

(54) APPARATUS AND METHODS FOR DELIVERY OF VARIABLE LENGTH STENTS

(75) Inventors: Sunmi Chew, San Jose, CA (US); Bernard Andreas, Redwood City, CA (US); Hanson S. Gifford, III, Woodside, CA (US); Ron French, Santa Clara, CA (US); Mark E. Deem, Mountain View, CA (US); Allan Will, Atherton, CA (US)

(73) Assignee: XTENT, Inc., Menlo Park, CA (US)

( * ) Notice: Subject to any disclaimer, the term of this patent is extended or adjusted under 35 U.S.C. 154(b) by 688 days.

(21) Appl. No.: 10/624,451

(22) Filed: Jul. 21, 2003

(65) Prior Publication Data

US 2004/0215331 A1 Oct. 28, 2004

Related U.S. Application Data

(63) Continuation-in-part of application No. 10/306,813, filed on Nov. 27, 2002, application No. 10/624,451, which is a continuation-in-part of application No. 10/306,620, filed on Nov. 27, 2002, now Pat. No. 7,147,656, application No. 10/624,451, which is a continuation-in-part of application No. 10/306,622, filed on Nov. 27, 2002, now Pat. No. 7,270,668.

(60) Provisional application No. 60/364,389, filed on Mar. 13, 2002, provisional application No. 60/336,967, filed on Dec. 3, 2001, provisional application No. 60/336,607, filed on Dec. 3, 2001, provisional application No. 60/336,767, filed on Dec. 3, 2001.

(51) Int. Cl.
*A61F 2/06* (2006.01)

(52) U.S. Cl. ................................. 623/1.12

(58) Field of Classification Search ............... 623/1.11, 623/1.12, 1.16; 606/108, 127, 192–198
See application file for complete search history.

(56) References Cited

U.S. PATENT DOCUMENTS 4,512,338 A 4/1985 Balko (Continued)

FOREIGN PATENT DOCUMENTS

EP 203945 B2 12/1986

(Continued)

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

(Continued)

*Primary Examiner*—Kevin T. Truong
(74) *Attorney, Agent, or Firm*—Townsend and Townsend and Crew LLP; J. Grainger, Esq.

(57) ABSTRACT

Blood vessels and other body lumens are stented using multiple, discreet stent structures, or continuous coiled or mesh stent structures. Stent structures may be balloon expandable or self-expanding and are delivered by a delivery catheter which is repositioned to spaced-apart delivery sights. By coating the stents with particular biologically active substances, hyperplasia within and between the implanted stents can be inhibited. An exemplary delivery catheter comprises a catheter body having a deployment mechanism for deploying one or more stents of selectable length into the vessel.

91 Claims, 24 Drawing Sheets

U.S. PATENT DOCUMENTS

| | | | |
|---|---|---|---|
| 4,564,014 A | 1/1986 | Fogarty et al. |
| 4,580,568 A | 4/1986 | Gianturco |
| 4,681,110 A | 7/1987 | Wiktor |
| 4,733,665 A | 3/1988 | Palmaz |
| 4,739,762 A | 4/1988 | Palmaz |
| 4,762,129 A | 8/1988 | Bonzel |
| 4,775,337 A | 10/1988 | Van Wagener et al. |
| 4,886,062 A | 12/1989 | Wiktor |
| 4,988,356 A | 1/1991 | Crittenden et al. |
| 4,994,066 A | 2/1991 | Voss |
| 4,994,069 A | 2/1991 | Ritchart et al. |
| 5,013,318 A | 5/1991 | Spranza, III |
| 5,040,548 A | 8/1991 | Yock |
| 5,092,877 A | 3/1992 | Pinchuk |
| 5,102,417 A | 4/1992 | Palmaz |
| 5,104,404 A | 4/1992 | Wolff |
| 5,135,535 A | 8/1992 | Kramer |
| 5,171,222 A | 12/1992 | Euteneuer et al. |
| 5,195,984 A | 3/1993 | Schatz |
| 5,217,495 A | 6/1993 | Kaplan et al. |
| 5,226,913 A | 7/1993 | Pinchuk |
| 5,246,421 A | 9/1993 | Saab |
| 5,273,536 A | 12/1993 | Savas |
| 5,282,824 A | 2/1994 | Gianturco |
| 5,300,085 A | 4/1994 | Yock |
| 5,312,415 A | 5/1994 | Palermo |
| 5,334,187 A | 8/1994 | Fischell et al. |
| 5,421,955 A | 6/1995 | Lau et al. |
| 5,458,615 A | 10/1995 | Klemm et al. |
| 5,478,349 A | 12/1995 | Nicholas |
| 5,490,837 A | 2/1996 | Blaeser et al. |
| 5,496,346 A | 3/1996 | Horzewski et al. |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,549,551 A | 8/1996 | Peacock, III et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,593,412 A * | 1/1997 | Martinez et al. ............ 623/1.11 |
| 5,607,444 A | 3/1997 | Lam |
| 5,607,463 A | 3/1997 | Schwartz et al. |
| 5,628,775 A | 5/1997 | Jackson et al. |
| 5,634,928 A | 6/1997 | Fischell et al. |
| 5,662,675 A | 9/1997 | Polanskyj Stockert et al. |
| 5,676,654 A | 10/1997 | Ellis et al. |
| 5,683,451 A | 11/1997 | Lenker et al. |
| 5,697,948 A | 12/1997 | Marin et al. |
| 5,702,418 A | 12/1997 | Ravenscroft |
| 5,709,701 A | 1/1998 | Parodi |
| 5,722,669 A | 3/1998 | Shimizu et al. |
| 5,723,003 A | 3/1998 | Winston et al. |
| 5,735,869 A | 4/1998 | Fernandez-Aceytuno |
| 5,749,848 A | 5/1998 | Jang et al. |
| 5,749,921 A | 5/1998 | Lenker et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,800,519 A | 9/1998 | Sandock |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,902,332 A | 5/1999 | Schatz |
| 5,919,175 A | 7/1999 | Sirhan |
| 5,922,020 A | 7/1999 | Klein et al. |
| 5,961,536 A | 10/1999 | Mickley et al. |
| 5,968,069 A | 10/1999 | Dusbabek et al. |
| 5,976,107 A | 11/1999 | Mertens et al. |
| 5,976,155 A | 11/1999 | Foreman et al. |
| 5,980,484 A | 11/1999 | Ressemann et al. |
| 5,980,486 A | 11/1999 | Enger |
| 5,980,514 A | 11/1999 | Kupiecki et al. |
| 5,980,552 A | 11/1999 | Pinchasik |
| 5,984,957 A | 11/1999 | Laptewicz, Jr. et al. |
| 6,007,517 A | 12/1999 | Anderson |
| 6,022,359 A | 2/2000 | Frantzen |
| 6,033,434 A | 3/2000 | Borghi |
| 6,039,721 A | 3/2000 | Johnson et al. |
| 6,042,589 A | 3/2000 | Marianne |
| 6,056,722 A | 5/2000 | Jayaraman |
| 6,066,155 A | 5/2000 | Amann et al. |
| 6,068,655 A | 5/2000 | Seguin et al. |
| 6,090,063 A | 7/2000 | Makower et al. |
| 6,090,136 A * | 7/2000 | McDonald et al. ......... 623/1.23 |
| 6,102,942 A | 8/2000 | Ahari |
| 6,106,530 A | 8/2000 | Harada |
| 6,120,522 A | 9/2000 | Vrba et al. |
| 6,123,712 A | 9/2000 | Di Caprio et al. |
| 6,123,723 A | 9/2000 | Konya et al. |
| 6,126,685 A | 10/2000 | Lenker et al. |
| 6,129,756 A * | 10/2000 | Kugler et al. ............... 623/1.27 |
| 6,143,016 A | 11/2000 | Bleam et al. |
| 6,165,167 A | 12/2000 | Delaloye |
| 6,179,878 B1 | 1/2001 | Duerig |
| 6,187,034 B1 | 2/2001 | Frantzen |
| 6,190,402 B1 | 2/2001 | Horton et al. |
| 6,196,995 B1 | 3/2001 | Fagan |
| 6,200,337 B1 | 3/2001 | Moriuchi et al. |
| 6,241,691 B1 | 6/2001 | Ferrera et al. |
| 6,251,132 B1 | 6/2001 | Ravenscroft et al. |
| 6,251,134 B1 | 6/2001 | Alt et al. |
| 6,254,612 B1 | 7/2001 | Hieshima |
| 6,254,628 B1 | 7/2001 | Wallace et al. |
| 6,258,117 B1 | 7/2001 | Camrud et al. |
| 6,267,783 B1 | 7/2001 | Letendre et al. |
| 6,273,895 B1 | 8/2001 | Pinchuk et al. |
| 6,273,913 B1 | 8/2001 | Wright et al. |
| 6,312,458 B1 | 11/2001 | Golds |
| 6,315,794 B1 | 11/2001 | Richter |
| 6,319,277 B1 | 11/2001 | Rudnick et al. |
| 6,325,823 B1 | 12/2001 | Horzewski et al. |
| 6,357,104 B1 | 3/2002 | Myers |
| 6,375,676 B1 | 4/2002 | Cox |
| 6,383,171 B1 | 5/2002 | Gifford et al. |
| 6,419,693 B1 | 7/2002 | Fariabi |
| 6,451,025 B1 | 9/2002 | Jervis |
| 6,451,050 B1 | 9/2002 | Rudakov et al. |
| 6,468,298 B1 | 10/2002 | Pelton |
| 6,468,299 B2 | 10/2002 | Stack et al. |
| 6,485,510 B1 | 11/2002 | Camrud et al. |
| 6,488,694 B1 | 12/2002 | Lau et al. |
| 6,511,468 B1 | 1/2003 | Gragg et al. |
| 6,520,987 B1 | 2/2003 | Plante |
| 6,527,789 B1 | 3/2003 | Lau et al. |
| 6,527,799 B2 | 3/2003 | Shanley |
| 6,555,157 B1 | 4/2003 | Hossainy |
| 6,575,993 B1 | 6/2003 | Yock |
| 6,582,394 B1 | 6/2003 | Reiss et al. |
| 6,592,549 B2 | 7/2003 | Gerdts et al. |

| | | |
|---|---|---|
| 6,599,296 B1 | 7/2003 | Gillick et al. |
| 6,602,282 B1 | 8/2003 | Yan |
| 6,605,062 B1 | 8/2003 | Hurley et al. |
| 6,645,547 B1 | 11/2003 | Shekalim et al. |
| 6,656,212 B2 | 12/2003 | Ravenscroft et al. |
| 6,666,883 B1 | 12/2003 | Seguin et al. |
| 6,679,909 B2 | 1/2004 | McIntosh et al. |
| 6,692,465 B2 | 2/2004 | Kramer |
| 6,702,843 B1 | 3/2004 | Brown |
| 6,712,827 B2 | 3/2004 | Ellis et al. |
| 6,712,845 B2 | 3/2004 | Hossainy |
| 6,723,071 B2 | 4/2004 | Gerdts et al. |
| 6,743,251 B1 | 6/2004 | Eder |
| 6,800,065 B2 | 10/2004 | Duane et al. |
| 6,849,084 B2 | 2/2005 | Rabkin et al. |
| 2001/0020154 A1 | 9/2001 | Bigus et al. |
| 2001/0020181 A1 | 9/2001 | Layne |
| 2001/0044595 A1 | 11/2001 | Reydel et al. |
| 2002/0037358 A1 | 3/2002 | Barry et al. |
| 2002/0107560 A1 | 8/2002 | Richter |
| 2002/0138132 A1 | 9/2002 | Brown |
| 2002/0151955 A1 | 10/2002 | Tran et al. |
| 2002/0156496 A1 | 10/2002 | Chermoni |
| 2002/0188343 A1 | 12/2002 | Mathis |
| 2002/0188347 A1 | 12/2002 | Mathis |
| 2003/0045923 A1 | 3/2003 | Bashiri et al. |
| 2003/0093143 A1 | 5/2003 | Zhao et al. |
| 2003/0114919 A1 | 6/2003 | McQuiston et al. |
| 2003/0114922 A1 | 6/2003 | Iwasaka et al. |
| 2003/0135266 A1 | 7/2003 | Chew et al. |
| 2003/0139796 A1 | 7/2003 | Sequin et al. |
| 2003/0139797 A1 | 7/2003 | Johnson et al. |
| 2003/0176909 A1 | 9/2003 | Kusleika |
| 2003/0199821 A1 | 10/2003 | Gerdts et al. |
| 2003/0225446 A1 | 12/2003 | Hartley |
| 2004/0087965 A1 | 5/2004 | Levine et al. |
| 2004/0093061 A1 | 5/2004 | Acosta et al. |
| 2004/0093067 A1 | 5/2004 | Israel |
| 2004/0098081 A1 | 5/2004 | Landreville et al. |
| 2004/0186551 A1 | 9/2004 | Kao et al. |
| 2004/0215165 A1 | 10/2004 | Coyle et al. |
| 2004/0215312 A1 | 10/2004 | Andreas |
| 2004/0249435 A1 | 12/2004 | Andreas et al. |
| 2005/0010276 A1 | 1/2005 | Acosta et al. |
| 2005/0038505 A1 | 2/2005 | Shuize et al. |
| 2005/0133164 A1 | 6/2005 | Andreas et al. |
| 2005/0149159 A1 | 7/2005 | Andreas et al. |
| 2005/0288763 A1 | 12/2005 | Andreas et al. |
| 2006/0229700 A1 | 10/2006 | Acosta et al. |
| 2006/0282147 A1 | 12/2006 | Andreas et al. |
| 2006/0282150 A1 | 12/2006 | Olson et al. |

FOREIGN PATENT DOCUMENTS

| | | |
|---|---|---|
| EP | 274129 B1 | 7/1988 |
| EP | 282143 | 9/1988 |
| EP | 0 505 686 | 9/1992 |
| EP | 0 533 960 | 3/1993 |
| EP | 0 596 145 | 5/1997 |
| EP | 947180 | 10/1999 |
| WO | WO 96/33677 | 10/1996 |
| WO | WO 97/46174 | 12/1997 |
| WO | WO 97/48351 | 12/1997 |
| WO | WO 99/01087 A1 | 1/1999 |
| WO | WO 00/15151 A1 | 3/2000 |
| WO | WO 00/32136 A1 | 6/2000 |
| WO | WO 00/41649 A1 | 7/2000 |
| WO | WO 00/62708 | 10/2000 |
| WO | WO 00/72780 | 12/2000 |
| WO | WO 01/70297 | 9/2001 |
| WO | WO 01/91918 | 12/2001 |
| WO | WO 03/022178 A1 | 3/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Colombo, "The Invatec Bifurcation Stent Solution" Bifurcation Stents: Novel Solutions, TCT 2003, Washington: Sep. 15-19, 2003, 24 pages total.

Lefevre et al. "Approach to Coronary Bifurcation Stenting in 2003," Euro PCR, (May 2003) 28 pages total.

"Stent". Definitions from Dictionary.com. Unabridged 9v1.01). Retrieved Sep. 22, 2006, from Dictionary.com website: <http://dictionary.reference.com/search?q=stent>.

Stimpson et al, Parallel Production of Oligonucleotide Arrays Using Membranes and Reagent Jet Printing, Bio Techniques 25:886-890 (Nov. 1998).

* cited by examiner

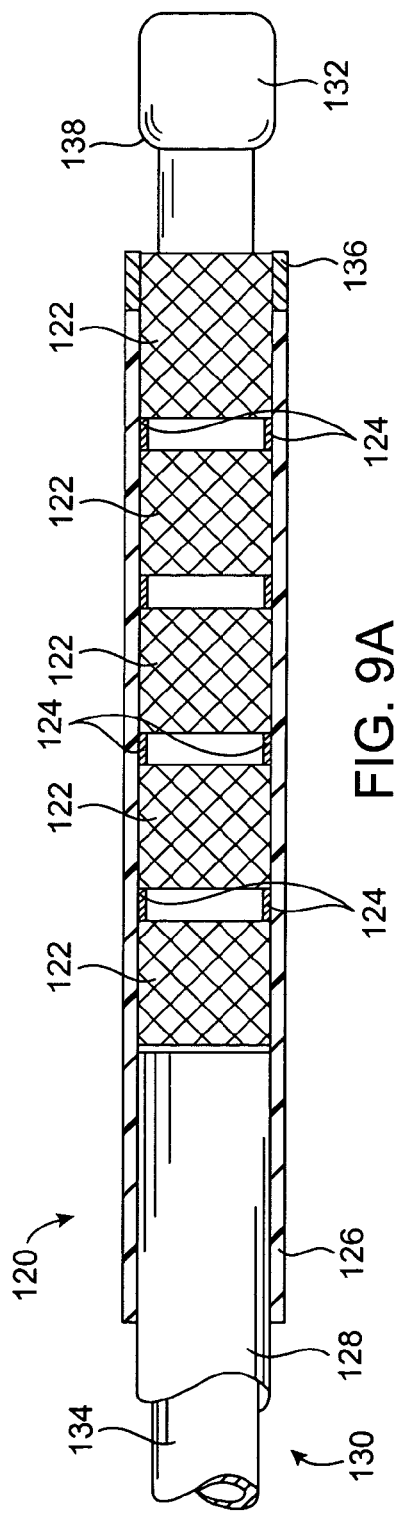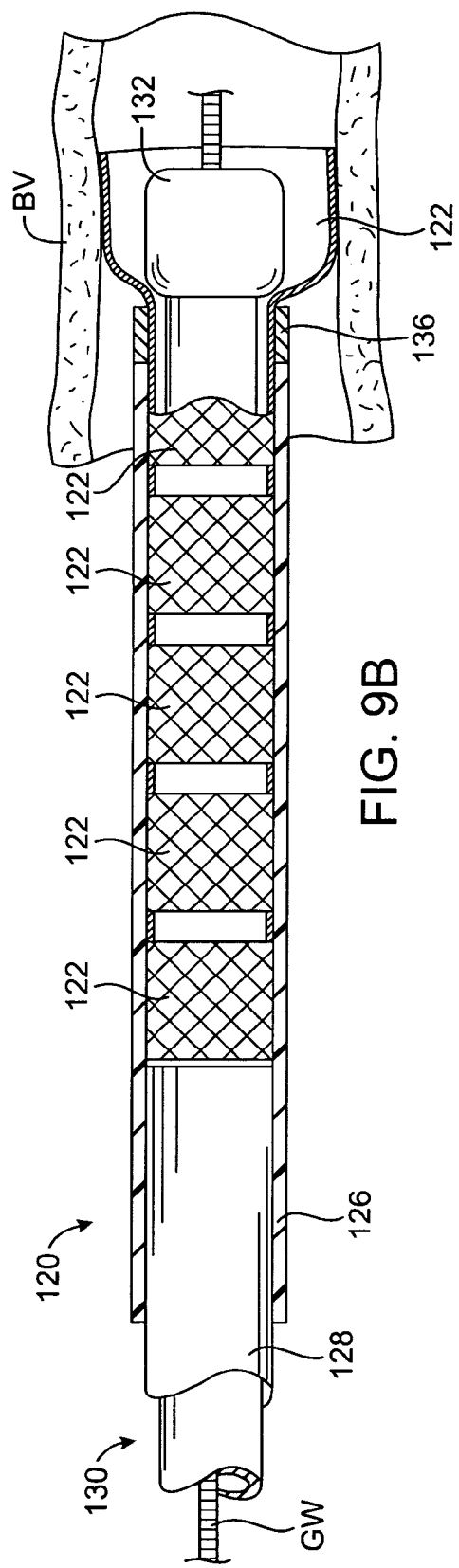

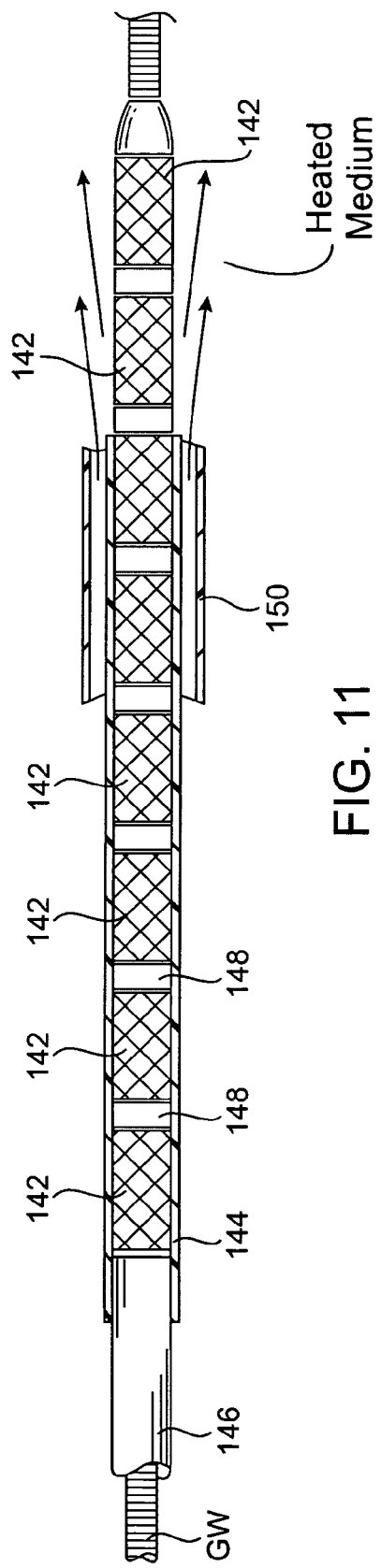

APPARATUS AND METHODS FOR DELIVERY OF VARIABLE LENGTH STENTS

CROSS-REFERENCES TO RELATED APPLICATIONS

The present application is a continuation-in-part of U.S. patent application Ser. No. 10/306,813, filed Nov. 27, 2002, which is a non-provisional of U.S. Patent Application Ser. Nos. 60/336,967 filed Dec. 3, 2001, and a non-provisional of U.S. Patent Application Ser. No. 60/364,389 filed on Mar. 13, 2002, the full disclosures of which are incorporated herein by reference. The present application is also a continuation-in-part of U.S. patent application Ser. No. 10/306,620, filed Nov. 27, 2002, now U.S. Pat. No. 7,147,656 which is a non-provisional of U.S. Patent Application Ser. No. 60/336,607, filed Dec. 3, 2001, the full disclosures of which are also incorporated herein by reference. The present application is also a continuation-in-part of U.S. patent application Ser. No. 10/306,622, filed Nov. 27, 2002, now U.S. Pat. No. 7,270,668 which is a non-provisional of U.S. Patent Application Ser. No. 60/336,767, filed Dec. 3, 2001, the full disclosures of which are also incorporated herein by reference.

BACKGROUND OF THE INVENTION

1. Field of the Invention

The present invention relates generally to medical devices and methods. More particularly, the present invention relates to apparatus and methods for independently delivering a plurality of luminal prostheses within a body lumen, such as a blood vessel.

Coronary artery disease is the leading cause of death and morbidity in the United States and Western society. In particular, atherosclerosis in the coronary arteries can cause myocardial infarction, commonly referred to as a heart attack, which can be immediately fatal or, even if survived, can cause damage to the heart which can incapacitate the patient.

While coronary artery bypass surgery can be an effective treatment for stenosed arteries resulting from atherosclerosis or other causes, it is a highly invasive, costly procedure, which typically requires substantial hospital and recovery time. Percutaneous transluminal coronary angioplasty, commonly referred to as balloon angioplasty, is less invasive, less traumatic, and significantly less expensive than bypass surgery. Heretofore, however, balloon angioplasty has not been considered as effective a treatment as bypass surgery. The effectiveness of balloon angioplasty, however, has improved significantly with the introduction of stenting which involves the placement of a scaffold structure within the artery which has been treated by balloon angioplasty. The stent inhibits abrupt reclosure of the artery and has some benefit in inhibiting subsequent restenosis resulting from hyperplasia. Recently, experimental trials have demonstrated that the coating of stents using anti-proliferative drugs, such as paclitaxel, can significantly reduce the occurrence of hyperplasia in angioplasty treated coronary arteries which have been stented with the coated stents.

While the combination of balloon angioplasty with drug-coated stents holds great promise, significant challenges still remain. Of particular interest to the present invention, the treatment of extended or disseminated disease within an artery remains problematic. Most stents have a fixed length, typically in the range from 10 mm to 30 mm, and the placement of multiple stents to treat disease over a longer length requires the suggestive use of balloon stent delivery catheters. Moreover, it can be difficult to stent an angioplasty-treated region of a blood vessel with the optimum stent length.

For these reasons, it would be desirable to provide improved stents, stent delivery systems, stenting methods, and the like, for the treatment of patients having coronary artery disease, as well as other occlusive diseases of the vasculature. In particular, it would be desirable to provide stents, delivery systems, and methods for the treatment of disseminated and variable length stenotic regions within the vasculature. For example, it would be desirable to provide a practical method which permits a physician to optimize the length of the treated vessel which is stented according to the nature of the disease. More specifically, it would be desirable to provide apparatus, systems, and methods for facilitating the delivery of multiple stents and other prostheses to blood vessels or other target body lumens. Such apparatus, systems, and methods should be suitable for delivery of individual stents or prostheses having very short lengths, typically as short as 3 mm or shorter, at multiple contiguous and non-contiguous locations within a body lumen for optimized treatment thereof.

In addition, it would be desirable to provide stents, delivery systems, and methods for the treatment of disseminated and variable length stenotic regions within the vasculature. For example, it would be desirable to provide methods which permit a physician to optimize the length of the treated vessel which is stented according to the nature of the disease, either by adjusting the stent length in situ or by placing multiple stents of the same or different lengths over the treatment region. It would be further desirable to provide a practical method which permits a physician to deliver extended lengths of braided prostheses to blood vessels and other body lumens. At least some of these objectives will be met by the inventions described hereinafter.

2. Description of the Background Art

U.S. Pat. No. 6,258,117 B1 describes a stent having multiple sections connected by separable or frangible connecting regions. Optionally, the connecting regions are severed after the stent structure has been implanted in the blood vessel. U.S. Pat. Nos. 5,571,086; 5,776,141; and 6,143,016 describe an expandable sleeve for placement over a balloon catheter for the delivery of one or two stent structures to the vasculature. U.S. Pat. No. 5,697,948 describes a catheter for delivering stents covered by a sheath. U.S. Pat. No. 6,190,402B1, describes a self-forming vascular implant. U.S. Pat. No. 6,258,117, describes a multiple section stent structure; and U.S. Pat. No. 5,895,398, describes a clot retrieval device having a deployable helical clot snare. U.S. Pat. No. 5,755,772 describes a tubular prosthesis and method for its implantation by positioning the prosthesis at a target site, and everting an end session to lock the stent after expansion has been completed; and U.S. Pat. No. 5,769,882 describes conformable tubular prostheses and their placement in blood vessels.

BRIEF SUMMARY OF THE INVENTION

The present invention provides methods and apparatus for prosthesis placement, such as stenting of body lumens, typically blood vessels, and more typically coronary arteries. The methods and systems will also find significant use in the peripheral vasculature, the cerebral vasculature, and in other ducts, such as the biliary duct, the fallopian tubes, and the like. The terms "stent" and "stenting" are defined to include any of the wide variety of expandable prostheses and scaffolds which are designed to be intraluminally introduced to a treatment site and expanded in situ to apply a radially outward force against the inner wall of the body lumen at that site. Stents and prostheses commonly comprise an open lattice structure, typically formed from a malleable or elastic metal. When formed from a malleable metal, the stents will typically be expanded by a balloon which causes plastic deformation of the lattice so that it remains opened after deployment. When formed from an elastic metal, including super elastic metals such as nickel-titanium alloys, the lattice structures will usually be radially constrained when delivered and deployed by releasing the structures from such radial constraint so that they "self-expand" at the target site. When the stent or lattice structures are covered with a fabric or polymeric membrane covering, they are commonly referred to as grafts. Grafts may be used for the treatment of aneurysms or other conditions which require placement of a non-permeable or semi-permeable barrier at the treatment site. The terms "prosthesis" and "prostheses" refer broadly to all radially expansible stents, grafts, and other scaffold-like structures which are intended for deployment within body lumens.

The stents and prostheses of the present invention may have any of a variety of common constructions, including helical structures, counterwound helical structures, expandable diamond structures, serpentine structures, or the like. Such conventional stent structures are well described in the patent and medical literature. Specific examples of suitable stent structures are described in the following U.S. patents, the full disclosures of which are incorporated herein by reference: U.S. Pat. Nos. 6,315,794; 5,980,552; 5,836,964; 5,527,354; 5,421,955; 4,886,062; and 4,776,337, the full disclosures of which are incorporated herein by reference. Preferred structures are described herein with reference to FIGS. 4 and 5.

According to the present invention, the stents which are deployed may have a length of 1 mm or greater, usually 2 mm or greater, and typically of 3 mm or greater, usually being in the range from 1 mm to 100 mm, typically from 2 mm to 50 mm, more typically from 2 mm to 25 mm, and usually from 3 mm to 20 mm. The use of such short stent lengths is advantageous since multiple stents are to be employed.

The methods and apparatus of the present invention will provide for the deployment of a plurality of stents or other prostheses, usually including at least two stents, from a common stent delivery catheter. Usually, the number of delivered stents will be in the range from 2 to 50, typically from 3 to 30, and most typically from 5 to 25. As more stents are placed on the delivery catheter, the individual stent length will often be somewhat less, although this is not necessarily the case in all instances. The multiple prostheses may be deployed individually or in groups of two or more at single or multiple spaced-apart locations in the body lumen or lumens.

In a first aspect of the present invention, a method for stenting an extending length of a body lumen comprises introducing a catheter carrying a plurality of, usually at least two, discrete stents to the body lumen. Usually, the introduction is percutaneous and, in the case of intravascular delivery, uses a conventional introduction technique, such as the Seldinger technique. After reaching a target location, at least a first stent is released from the catheter at that first location. The catheter is then repositioned to a second location, and at least a second stent is released from the catheter at the second location. The catheter is then repositioned to a third location, and at least a third stent is released from the catheter at the third location In addition to deploying stents and other prostheses at spaced-apart locations within a blood vessel or other body lumen, the methods and apparatus in the present invention can be used for delivering one, two, three, or more discrete stents or other prosthesis segments contiguously at a single location within the body lumen. In this way, the length of the prosthesis which is implanted can be selected and modified to accommodate the length of the vessel to be treated. It will be appreciated that with systems which carry 10, 20, 30 or more quite short prostheses or prosthesis segments, the length of the lumen being treated can be tailored very closely from very short to very long with the selectable intervals depending on the length of the prosthesis or prosthesis segment.

The deployment steps can, of course, be repeated a sufficient number of times so that all or at least more of the stents carried by the delivery catheter are delivered to and deployed within the body lumen. A particular advantage of this delivery method is that the discrete stents may be distributed along extended lengths of the body lumen, typically in the range from 1 cm to 2 cm, often in the range from 1 cm to 5 cm, and in many instances even longer. Additionally, the stents may be delivered so as to avoid side branches or other regions where placement of the stent is undesirable. Moreover, with the use of drug-coated stents, it may be possible to place the stents apart by discrete distances, typically from one-half to one millimeter (mm), while still achieving vessel patency and hyperplasia inhibition.

Releasing of the stents from the catheter may be achieved using a balloon to cause balloon expansion of the stent. Alternatively, release of the stent may be achieved by radially constraining an elastic or self-expanding stent within a lumen of the delivery catheter and selectively advancing the stent from the catheter and/or retracting the catheter from over the stent. In one embodiment, a sheath over the stents includes a valve member, or "stent valve," which allows stents to be separated so that a balloon can more accurately inflate deployed stents while other stents remain within the sheath.

In preferred embodiments, the stents are coated with at least one agent, such as an agent which inhibits hyperplasia. The agent may be biologically active or inert. Particular biologically active agents include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Biologically inert agents include polyethylene glycol (PEG), collagen, polyglycolic acids (PGA), ceramic material, titanium, gold and the like.

In another aspect, the present invention comprises catheters and apparatus for stenting extended lengths of a body lumen, particularly a blood vessel. The catheters comprise a catheter body having a proximal end and a distal end. At least two discrete stents are carried at or near a distal end of the catheter body. By "discrete," it is meant that the stents are unconnected and can be deployed from the catheter in an unattached manner. (The delivery of attached prostheses is described below.) Deployment of such discrete stents permits the individual stents to be placed at spaced-apart target locations or immediately adjacently within the blood vessel or other body lumen. The catheters further comprise deployment means for deploying the individual stents from the catheter body. For example, the deployment means may comprise one or more balloons for placement and radial expansion of the stents. Alternatively, the deployment means may comprise a pusher or other device for advancing self-expanding stents from the distal end of the catheter body and/or a sheath for selectively retracting over the stents to permit self-expansion. In exemplary embodiments, the catheters will carry at least two discrete stents, at least five discrete stents, and as many as 10 discrete stents, or in some cases, as many as 30 or more discrete stents.

In a particular embodiment, the catheter comprises a single balloon which is reciprocatively mounted within the catheter body and adapted for receiving individual stents thereover. A pusher or other device for successively and controllably loading individual or multiple stents over the balloon is also provided. In this way, the catheter may carry multiple stents and employ the single balloon for positioning and expansion of the stents.

In further embodiments, the stents of the present invention are composed at least partly of a bioabsorbable material, such as polyethylene glycol (PEG), collagen, gelatin, polyglycolic acids (PGA), polylactic acids (PLA), and the like. Optionally, one or more bioactive substances are dispersed in the bioabsorbable material such that the bioactive substance will be released over time as the bioabsorbable material degrades. In a particular embodiment, the bioabsorbable material is formed on or within a scaffold composed on a non-bioabsorbable material, typically stainless steel, Nitinol™, or other conventional stent metal material. Other materials, such as gold (e.g., pure or nearly pure gold), platinum, or the like, may also be used.

In a further aspect of the present invention, a catheter for delivering a plurality of expansible prostheses to a body lumen comprises a catheter body, a sheath, and a plurality of radially expansible prostheses. The catheter body has a proximal end and a distal end, and the sheath is coaxially disposed over the catheter body with the prostheses positionable in an annular space between the inside of the sheath and the exterior of the catheter body. The sheath is preferably retractable relative to the catheter body so that the prostheses may be advanced beyond a distal end of the sheath. Usually, the catheter will further comprise a pusher tube disposed coaxially over the catheter body and within an interior lumen of the sheath. A distal end of the pusher tube will engage a proximal end of the proximal-most prosthesis so that the pusher tube can be distally advanced relative to the sheath to selectively push or deploy individual prostheses from the sheath. Often, such deployment is achieved by holding the pusher tube and prostheses substantially stationary relative to the body lumen while the sheath is retracted proximally to release or deploy the prostheses.

Usually, at least a distal portion of the sheath will have a greater column strength than that of a distal portion of the catheter body. Additionally or alternatively, the pusher tube may also have a greater column strength than a distal portion of a catheter body. By providing column strength in the outer most portion of the catheter, i.e., the sheath, and optionally the pusher tube, the overall column strength of the catheter can be increased with a minimum increase in its diameter or profile. It will be appreciated that low profile catheters are highly advantageous for accessing remote regions of the vasculature, particularly the small coronary and cerebral arteries. Using the preferred constructions of the present invention, catheters having diameters 2 mm or less, and in some instances as low as 1 mm or less, can be achieved. The constructions will, of course, also be suitable for larger diameter catheters for use in the peripheral and other larger blood vessels.

The catheter of the present invention will preferably carry at least two prostheses, more preferably carrying at least three prostheses, and often carrying a greater number of prostheses as set forth above in connection with other embodiments. The prostheses will typically be arranged in an end-to-end manner either with or without a physical linkage therebetween. The physical linkage may comprise a frangible component which must be mechanically broken or alternatively may comprise a pair of coupling elements which fit together and which may be separated without any material breakage. Frangible coupling elements will usually comprise a strut, bar, spring, or similar connecting link and will optionally be scored, notched, or otherwise adapted to break along a particular line when a suitable mechanical force is applied. Exemplary separable coupling elements include male and female elements, such as a rod and tube which may be axially separated, a tab and receptacle which may be radially separated, and the like.

In a specific embodiment of the catheter, the catheter body may comprise an expansion element, such as an inflatable balloon, near its distal end. The expansion element will be positionable distal to the retractable sheath so that it can be used to regularly expand one or more of the prostheses. For example, the inflatable balloon may carry multiple prostheses on its outer surface so that sheath retraction can expose one, two, three, or more of the prostheses. The remaining prostheses will continue to be covered by the sheath. When inflating the balloon, however, only that portion of the balloon and those prostheses carried on the exposed portion of the balloon will be inflated. The remaining (proximal) portion of the balloon will continue to be constrained by the sheath so that neither the balloon nor the prostheses covered by the sheath will be expanded. In this way, any preselected number of the individual prostheses may be expanded at one time, while the remaining prostheses are protected and unexpanded, remaining available for subsequent expansion using the balloon.

Alternatively or in addition to the balloon, the catheter body may comprise a heater for selectively heating prostheses which have been advanced distally beyond the sheath. For example, the catheter body may have a lumen for delivering a heated medium, such as heated saline, intravascularly to heat and expand stents or other prostheses formed from suitable heat memory alloys (as described in more detail below). Alternatively, a separate exterior guide catheter or other tube may be used for delivering such a heated medium to effect expansion of the prostheses. As a third alternative, a powered heating element, such as a radio frequency heater, electrical resistance heater, or laser-heated element, may be provided on the catheter body for directly heating the exposed prostheses.

For the delivery of individual prostheses or stents which are joined by frangible or breakable links, as discussed above, it will often be desirable to provide a shearing mechanism on the catheter. The shearing mechanism will usually be mechanical, but could also be electrolytic, ultrasonic, or chemical. In the exemplary embodiments, the shearing mechanism comprises a first shearing element on a distal region of the catheter body and a second or mating shearing element on a distal region of the sheath. The prostheses may be advanced from the sheath while the shearing mechanism on the catheter body is distally advanced (leaving a space or opening for prosthesis deployment). After a desired number of prostheses have been deployed, the catheter body may be retracted relative to the sheath in order to close the shearing elements to sever the link(s) between the advanced prostheses and those prostheses which remain within the sheath. In other cases, the shearing mechanism could be an electrode for inducing electrolytic breakage of the link, an ultrasonic transducer for mechanically degrading a susceptible link (i.e. a link having a resonant frequency which corresponds to the ultrasonic transducer), a luminal port for releasing a chemical agent selected to chemically degrade the link, or the like.

In a further alternative embodiment, a catheter constructed in accordance with the principles of the present invention comprises a pusher tube, a plurality of radially expansible prostheses arranged end-to-end and extending distally of the distal end of the pusher tube, and a sheath disposed coaxially over the pusher tube and the prostheses. Optionally, but not necessarily, this embodiment will include a catheter body disposed coaxially within the pusher tube and prostheses. By retracting the sheath proximally relative to the pusher tube, individual ones or groups of the prostheses will be exposed and deployed. The catheter body may be used in any of the ways described previously in order to effect or control deployment of the prostheses. Optionally, the pusher tube, the sheath, or both, may have a greater column strength than the catheter body when the catheter body is employed.

Systems of detachable expansible prostheses according to the present invention include a plurality of ring-like radially expansible prostheses arranged end-to-end along an elongate axis. At least one pair of coupling elements join each pair of adjacent prostheses, where the coupling elements physically separate without fracture in response to axial tension or differential radial expansion. The coupling elements, however, remain coupled when subjected to axial compression such as may occur as the prostheses are axially advanced within a body lumen or elsewhere. The prostheses may be composed of a malleable material so that they will be expansible in response to an internally applied radially expansive force, such as a balloon expansion force applied by a balloon carried by the catheter body in any of the prior embodiments of the present invention. Alternatively, the prostheses may be composed of a resilient material, such as spring stainless steel, nickel-titanium alloy; or the like, so that they may be "self-expanding," i.e. expand when released from radial constraint. As a third alternative, the prostheses may be composed of a heat memory alloy, such as a nickel titanium alloy, so that they may be induced to expand upon exposure to a temperature above body temperature. Materials suitable for forming each of these three types of prostheses are well described in the patent and medical literature.

In specific examples of the systems, the coupling elements may be male and female so that they decouple upon the application of an axial force. For example, the coupling elements may be a rod and a tube having a central passageway for receiving the rod. Alternatively, the coupling elements may be configured to decouple upon differential radial expansion. For example, a first coupling element may extend from the end of a first prostheses and have an enlarged portion or end. By providing a cut-out in the adjacent prostheses having a periphery which matches the periphery of the extension on the first prostheses, coupling elements can be mated and locked together. The locking will resist axial separation, but permit radial separation when one of the prostheses is radially expanded.

The systems of prostheses just described may be preferably employed with any of the catheter delivery systems described previously.

The present invention further provides methods for stenting extended lengths of the body lumen, where the methods comprise introducing a catheter carrying a plurality of radially expansible prostheses to a target site within the body lumen. The prostheses are arranged end-to-end and are covered by a sheath. The prostheses are then deployed by retracting the sheath relative to the prostheses by a first preselected distance to uncover a first predetermined number of the prostheses. After retraction of the sheath, a first predetermined number of prostheses, which may be anywhere from one up to the entire number of prostheses being carried, are radially expanded at the target site within the target site of the body lumen.

Prosthesis expansion may be achieved in a variety of ways. In a first instance, the prostheses are expanded by inflating a balloon within the particular prosthesis to be expanded. For example, a single balloon may be disposed under all the prostheses, with the sheath retracted to expose only those prostheses to be deployed. When the balloon is expanded, the balloon will expand the exposed prostheses, with expansion of the prostheses which remain covered being restrained by the sheath. By further retracting the sheath, the previously undeployed prostheses may then be deployed. Optionally, the prostheses are advanced (or at least axially restrained relative to the sheath) by a pusher tube which engages a proximal end of the proximal-most prosthesis.

As an alternative to balloon expansion, the uncovered prostheses may be expanded by exposure to heat. The heat may be applied by directing a heated medium to the prostheses, directing electrical energy through the prostheses, and/or energizing a heating element positioned adjacent to the uncovered prostheses.

In preferred aspects of the methods of the present invention, the body lumen will be a blood vessel, preferably a coronary artery, a cerebral artery, or other small artery. The prostheses will preferably be coated with biologically active or inert agent, such as an agent selected to inhibit hyperplasia, more specifically being any of the particular agents set forth hereinabove.

The catheters of the present invention will comprise a number of coaxial components, such as sheaths, pusher tubes, catheter bodies, and the like. While it will often be described that stents or other prostheses are advanced distally from the sheath, such description will apply to sheaths which are retracted proximally relative to the prostheses to effect the release. Thus, all descriptions of direction are meant to be relative.

The present invention further provides for improved methods, apparatus, and systems for delivering prostheses to body lumens, particularly stents and grafts to blood vessels in the arterial and venous vasculature. The prostheses comprise scaffold structures formed from linearized elements, typically metal wires having a round diameter, but also including ribbons, multifilar cables, braided structures, composite structures, wires having non-circular cross-sections, and the like. By "linearized element," it is meant that the structural component will be capable of assuming a linearized configuration while the scaffold is being delivered. Most simply, the linearized element will have a non-linear configuration when unconstrained and will assume the linearized configuration when subjected to radial or axial constraint. In such instances, the linearized element will be formed so that it has a "memory" of the non-linear configuration but can be linearized by applying compressive or axial stress. In the exemplary embodiment, the linearized element has a helical memory. When constrained within the lumen of a delivery device, the linearized element assumes a generally straight configuration. When advanced outwardly from the constrained lumen, however, the linearized element returns to its helical configuration. A number of metals will have efficient elasticity to be able to shift between the linearized and non-linear configurations. Some of the metals include spring stainless steels, such as MP35N, Elgiloy, as well as superelastic alloys, such as nickel-titanium alloys, e.g. Nitinol™ alloy.

While the presently preferred linearized element will be formed from an elastic metal, one skilled in the art will appreciate that a variety of other metal and non-metal materials could be used to form such elements. For example, the elements could be formed from malleable metals, such as malleable stainless steel alloys, where the linearized element is then deformed into the non-linear configuration as it is advanced from the delivery device, e.g., by passing the linearized element over a shaping mandrel in the delivery device. Alternatively, the linearized element could be formed from a heat memory alloy, where the element is heated in situ after deployment in order to effect the change in shape from linear to non-linear. In addition, resilient and malleable polymeric and other non-metal materials might find use. These technologies, as well as others, for changing the shape of metal and non-metal structures within body lumens, are well described in the technical and medical literature.

The linearized elements of the present invention will be capable of assuming a variety of non-linear configurations. While helical non-linear configurations are presently preferred, it will be appreciated that serpentine, zigzag and other irregular configurations would also be suitable for at least some of the intended purposes of the present invention. Moreover, while it will generally be preferred to form the linearized elements from wire, most usually wire having a circular cross-section, it will also be possible to form the linearized elements from ribbons, flat sheets of material, and other conventional techniques. For example, serpentine or zigzag non-linearized elements could be formed from flat sheets of appropriate metal, e.g. by laser cutting, chemical etching, or the like. For example, a flat sheet could be configured to assume a desired tubular geometry.

Methods according to the present invention for delivering prostheses to a body lumen comprise introducing a delivery device to an interior of the body lumen, typically the lumen of a blood vessel, where the device carries the linearized element, as discussed above. The element is deployed by advancing the element relative to the delivery device within the interior of the body lumen so that the element assumes its non-linear configuration across the surface region of the interior as the element is advanced. The element is then released from the delivery device after it has assumed its non-linear configuration. Release may be effected by selectively severing the element after a desired length of the element has been reached. Alternatively, the delivery device may carry a plurality of linearized elements, each having a desired length so that each individual element is released after its entire length has been advanced from the delivery device.

Advancing the linearized element relative to the delivery device may comprise drawing the delivery device proximally relative to the body lumen while pushing the linearized element from the delivery device, typically using an internal pusher element. In such instances, the pusher rod will usually be held in a generally stationary relationship to the body lumen, while the delivery device is retracted proximally relative to both the body lumen and the pusher rod. In this way, the linearized element will deploy within the body lumen, while assuming its non-linear configuration, with little or no relative movement relative to the luminal wall. This is desirable since any movement of the linearized element against the luminal wall may cause injury, particularly in arteries and other blood vessels.

In order to even further reduce movement of the deploying linearized element against the vessel wall, and thus reducing the risk of trauma to the vessel wall, it will often be desirable to control the deployment to offset the foreshortening of the linearized element as it is deployed. It will be appreciated that when a linearized element assumes a non-linear configuration, such as a helical configuration, the absolute length of the element will shorten. In the case of helical elements, the shortening will be quite significant, typically from 80 percent to 99 percent, depending on the pitch of the helix which is released. In order to minimize motion of the element against the vessel wall as it is deployed, it is therefore desirable to move the delivery device approximately at a rate substantially equal to the axial progress of the deployed helix within the body lumen (which will be much less than the absolute length of the linearized element which is being expelled). Thus, the pusher rod will be moving in a distal direction which is more rapid than the proximal withdrawal of the delivery device. Moreover, it will be further desirable to rotate the delivery device so that the deploying "helical" element is not caused to rotate within the vessel. Thus, three separate parameters of the deployment will need to be controlled to minimize the relative motion of the helical element against the blood vessel wall. First, the delivery device will be withdrawn proximally at a rate equal to the axial rate of deployment of the helix within the blood vessel. Second, the pusher rod will be distally advanced at a rate equal to the linear deployment rate of the helix within the deployment device. Finally, rotation of the delivery device will be controlled to counteract any tendency of the delivery device to rotate the helix as it is being deployed. All three of these deployment parameters may be manually controlled by the physician by observing the deployment under fluoroscopic imaging. Alternatively, programmable systems may be provided to automatically deploy and control the element deployment.

In a specific aspect of the method of the present invention, the pitch of the helical element may be controlled by adjusting the rate of drawing the delivery device proximally and/or advancing the linearized element from the delivery device. While the helical configuration of the linearized device will usually have a preferred or natural pitch, the actual pitch within the blood vessel or the body lumen may be controlled to a certain degree by adjusting its rate of advancement and the withdrawal rate of the delivery device to adjust the pitch. Usually, the delivery device will be rotated in order to further control the release geometry of the linearized element.

In other specific aspects of the method of the present invention, the prostheses are selectively deployed to traverse desired lengths of the vasculature or other body lumen. The covered length can be controlled in either or both of two ways, First, when the delivery device has the ability to sever the linearized element, the treating physician can control the length of the prostheses by simply starting at a first target location, deploying the prostheses as described above (optionally with control of pitch in a helical prostheses), and severing the prostheses from the delivery device when a desired end location has been reached.

Additionally, the length of the vessel to be treated may be controlled by delivering multiple helical or other prostheses at selected and distributed portions of the luminal wall. Again, the treating physician will choose a beginning point within the body lumen and then deliver a prostheses over a selected length of the body lumen from that point. One, two, three, four or more additional segments of the prostheses may then be deployed.

Thus, the methods and apparatus of the present invention can be used to treat both short and long diseased segments within the vasculature and other body lumens. Usually, the treated regions will have a length of at least 10 mm and may have a length up to 60 mm and in some instances 100 mm or longer. Typically, when using only a single deployed prostheses, the treated lengths will be from 10 mm to 50 mm, usually from 10 mm to 30 mm. When using multiple prostheses, the lengths may be much greater, typically from 20 mm to 100 mm, more often from 20 mm to 60 mm.

As a further option, the linearized elements of the present invention may be coated, loaded, or otherwise coupled to or with an active substance intended to enhance the selected therapy. Linearized elements intended for treating blood vessels and other body lumens may be coated with substances intended to inhibit cellular proliferation, inflammation, or other conditions. Exemplary active substances include anti-neoplastic drugs such as paclitaxel, methotrexate, and batimastal; antibiotics such as doxycycline, tetracycline, rapamycin, and actinomycin; immunosuppressants such as dexamethosone, methyl prednisolone, nitric oxide sources such as nitroprussides; estrogen; estradiols; and the like.

The present invention further comprises catheters and other apparatus for delivering helical prostheses. The catheters comprise a catheter body having a proximal end, a distal end, and at least one lumen through at least a portion thereof. A linearized element is disposed in the lumen, and the mechanism for advancing and releasing at least one length of the linearized element from the lumen is provided. As described above, the linearized elements will assume a non-linear configuration when advanced and released from the catheter body. Usually, the advancing and releasing mechanism will comprise a severing mechanism to selectively cut the linearized element after a desired length has been released. Alternatively, the catheter may carry a plurality of linearized elements which are divided or cut into discrete lengths prior to deployment. Thus, the discrete lengths may be released after they are fully advanced from the lumen of the catheter body. In the latter case, the catheter body may carry from two to twenty discrete elements, typically from three to ten discrete elements.

In a further aspect, the stents of the present invention will comprise evertible structures which radially expand upon eversion to assume a non-collapsible diameter which remains in place within the body lumen to support the luminal wall. Typically, the evertible stent structures will comprise braided structures, but other structures, such as counterwound helices, will also be capable of eversion. In some instances, laser cut helical and other patterned metal tubes, particularly those formed from nickel titanium and other shape memory alloys, may be used. Thin wall tubes formed from polymeric materials, such as polyethylene terephthalate (PET), expanded polytetrafluoroethyolene (e PTFE), may also find use, even without patterning.

The braided and other evertible stent structures of the present invention may be formed from metals, including both malleable metals and elastic metals, such as shape memory metals, as well as from polymeric materials. Usually, the braided structures will comprise individual ribbons of the desired material which are interwoven to form a braid so that the braid may be axially elongated to assume a narrow diameter configuration and thereafter be everted to assume a larger diameter configuration. By "evert" it is meant that a leading edge of the prosthesis is turned outwardly and backwardly relative to the narrow diameter portion thereof. In the preferred methods and apparatus of the present invention, as described in more detail below, such eversion will be achieved by initially holding the prosthesis in its narrow diameter configuration with the leading portion everted and fixed to an outer portion of a catheter. This leading portion is referred to as the "fixed end." The remainder of the prosthesis which remains in its narrow diameter configuration is held within a passage or lumen of a delivery catheter, and means are provided for pushing the "advancable end" of the prosthesis which is in the lumen forwardly relative to the fixed end. In this way, the leading edge of the prosthesis moves forward continuously relative to the fixed end as it everts radially outwardly.

The use of such braided and other evertible prostheses provides a number of advantages. For example, the braided structure is highly flexible, particularly in its narrow diameter configuration, allowing the introduction of relatively long stent segments without significantly limiting the ability of the delivery catheter to pass through torturous regions of the vasculature or other body lumens. Additionally, by everting the prosthesis so that its outer portion remains stationary relative to the fixed end (and thus also relative to the delivery catheter), the stent will be able to pass through relatively small body lumens since it advances much like a tractor tread in moving forwardly through the lumen. In the case of vascular treatments, the stents of the present invention will usually be used following other primary interventions, such as angioplasty, atherectomy, aneurysm repair, or the like. It will be possible, however, in certain instances, to deliver the stent without prior intervention because of the ability to advance through tight lesions and to dilate the lesion as it passes therethrough.

Usually, the methods and apparatus of the present invention will be used to deliver a single stent having a predetermined length. In other instances, however, it will be possible to provide a means for severing the stent on the catheter itself. In such cases, the methods and apparatus of the present invention will be capable of delivering variable lengths of stent depending on the nature and extent of the disease being treated. That is, the apparatus will be used to deliver the stent under fluoroscopic or other observation, and after a desired length of stent has been deployed, the deployed length can be severed from the length which remains carried within the delivery catheter.

In one aspect, methods according to the present invention thus comprise positioning a tubular prosthesis at a target site within a body lumen. The prosthesis is then everted so that an inside surface is exposed radially outwardly and advanced over a length of the wall of the body lumen. Usually, positioning comprises introducing a delivery catheter having a passage which carries the tubular prosthesis at least partly in a radially collapsed configuration. Everting usually comprises pushing the tubular prosthesis from the catheter so that a leading portion of the prosthesis everts and radially expands as it exits the catheter or passage. This is usually accomplished by forwardly advancing a portion of the catheter to push the prosthesis from the catheter. In a preferred aspect of the present invention, an advancable segment of the prosthesis is carried in the passage in the radially collapsed configuration. A fixed end of the prosthesis is held stationary relative to the catheter in a partially everted configuration. Everting then comprises pushing a proximal end (i.e., an end or portion of the prosthesis which is radially collapsed within the delivery catheter) to cause a middle portion of the prosthesis to progressively evert and advance distally relative to the fixed end. In the case of braided prostheses, the braided structure will shorten as the radius expands so that the "advancable" proximal end prosthesis is pushed forward at a rate which is faster than the rate at which the everted prosthesis covers the wall of the body lumen. In preferred embodiments, the prosthesis releases an active substance which inhibits hyperplasia after the prosthesis has been placed in the body lumen.

In a further aspect of the present invention, apparatus for delivering a prosthesis to a body lumen comprise a catheter having a passage. A tubular prosthesis is carried at least partially in the passage in a radially collapsed configuration. A mechanism for advancing the prosthesis from the passage so that the prosthesis everts and radially expands as it is advanced is also provided. The tubular prosthesis is preferably a braided tube, and the braided tube is composed at least partly from a material selected from the group consisting of stainless steel, shape memory alloys, and polymer resins. Optionally, the prosthesis may carry a source of an active substance, such as a substance which inhibits hyperplasia. Exemplary active substances include anti-neoplastic drugs such as paclitaxel, methotrexate, and batimastal; antibiotics such as doxycycline, tetracycline, rapamycin, and actinomycin; immunosuppressant such as dexamethosone, methyl prednisolone, nitric oxide sources such as nitroprussides; estrogen; estradiols; and the like. Such active substances may be carried on the prosthesis in a variety of ways. For example, they may be coated by spraying, dipping, painting, or the like. Alternatively, they may be stored in reservoirs, i.e., etched depressions or spaces within the prosthesis structure. In the latter case, delivery is often controlled using a microporous, macroporous, or diffusible rate-controlling membrane. In other instances, the active substances may be incorporated in porous or nonporous polymeric layers which are incorporated over or within the braided or other evertible stent structures.

In an exemplary apparatus of the present invention, the fixed end of the prosthesis is everted over an outside surface of the catheter. An advancable end of the prosthesis remains in the catheter passage. A pusher to push the middle of the prosthesis distally relative to the catheter to evert and advance a leading edge of the prosthesis relative to the fixed end is also provided. Optionally, a central tube is disposed inside of the collapsed portion of the prosthesis, and further optionally, the central tube may be advancable together with the pusher to evert the prosthesis.

In still another aspect, the invention provides apparatus and methods for deploying stents of variable length into a vessel. An exemplary apparatus for variable length stent deployment comprises a flexible catheter body having a proximal end and a distal end adapted for positioning in the vessel. Stenting structure is releasably held by the catheter body in an unexpanded configuration and is movable from the unexpanded configuration to an expanded configuration adapted to engage a wall of the vessel. The catheter further includes a deployment mechanism coupled to the catheter body adapted to deploy a deployable portion of the stenting structure. The deployable portion is released into the vessel in the expanded configuration while a remaining portion of the stenting structure remains releasably held by the catheter body in the unexpanded configuration. Advantageously, the deployment mechanism enables the deployment of a deployable portion having a selectable length suited to match the length of the vessel or lesion to be treated.

In an exemplary embodiment, the stenting structure comprises a plurality of stent segments, and the deployment mechanism is adapted to select one or more of the stent segments for inclusion in the deployable portion. The stent segments in the deployable portion are preferably deployed simultaneously. The apparatus may further include a constraining element for constraining expansion of a selected stent segment, typically being a sheath disposed over the selected stent segment.

In one embodiment, the deployment mechanism comprises an expandable member on the catheter body, the deployable portion of the stenting structure being positionable over the expandable member for expansion thereby. Preferably, the length of the expandable member can be adjusted according to the length of the deployable portion, for example by sliding a sheath over a portion of the expandable member to constrain expansion of that portion. The apparatus may further include a stent positioner for moving a selected portion of the stenting structure relative to the expandable member.

The apparatus may further include a valve member on the catheter body adapted to separate the deployable portion from the remaining portion. In an exemplary embodiment, the valve member is disposed on a sheath extending over the stenting structure.

In a preferred embodiment, the deployable portion of the stenting structure is deployable from a fixed position relative to the distal end of the catheter body. For example, the stenting structure may have a leading end closest to the distal end of the catheter body, and the deployable portion of the stenting structure extends proximally a selectable length from the leading end thereof. In some embodiments, the deployable portion is deployed distally from the distal end of the catheter body. Alternatively, the deployable portion is deployed radially by an expandable member.

In an alternative aspect, the stenting structure is continuous throughout the length thereof, and the deployment mechanism is adapted to separate the deployable portion of the stenting structure from a remaining portion of the stenting structure at a selectable location. In an exemplary embodiment, the deployment mechanism is adapted to sever the stenting structure at the selectable location. Usually the deployable portion is severed from the remaining portion of the stenting structure following deployment from the catheter into the vessel. In one embodiment of a continuous stenting structure, the stenting structure is a coil. Alternatively, the stenting structure may be a mesh. Usually in these embodiments, the stenting structure will be self-expanding.

In a further aspect of the invention, a method of deploying a stent of selectable length in a vessel comprises: endovascularly positioning a catheter in the vessel, the catheter having a distal end and stenting structure releasably disposed therein; positioning a deployable portion of the stenting structure in a position suitable for deployment from the catheter; determining a desired stent length; adjusting the length of the deployable portion to be the desired stent length; and releasing the deployable portion from the catheter into the vessel, wherein the deployable portion expands to engage a wall of the vessel while a remaining portion of the stenting structure remains releasably disposed in the catheter.

In a preferred aspect, adjusting the length of the deployable portion comprises positioning a first portion of the stenting structure shorter than the desired stent length in a position in the catheter for release into the vessel, and positioning an additional portion of the stenting structure in the catheter adjacent to the first portion for release therewith. This enables the length of the deployable portion to be precisely tailored in situ to the length of the lesion to be treated. Usually, the deployable portion will be separated from the remaining portion by axially moving the deployable portion relative to the remaining portion (or moving the remaining portion relative to the deployable portion).

Advantageously, the method facilitates the deployment of multiple stents of various lengths without removing the catheter from the patient's vasculature. For example, the method may further include the steps of determining a second stent length; selecting a second portion of the stenting structure having the second stent length; and releasing the second portion in the vessel, wherein the second portion expands to engage a wall of the vessel. Of course, two, three, four or more stents may be deployed from the catheter in succession, all of the same or differing lengths depending on the size of the lesions to be treated.

Preferably, the deployable portion and the second portion are deployed from a fixed position relative to the distal end of the catheter. To enable this, the stenting structure is axially movable along the catheter to the fixed position of deployment. Typically, the position of deployment will be at the distal end of the catheter and the stenting structure will have a leading end closest to the distal end of the catheter. The step of adjusting the length of the deployable portion will then comprise selecting a desired length of the stenting structure extending proximally from the leading end thereof.

In some embodiments, the deployable portion will be released by expanding an expandable member. Preferably, the length of the expandable member (or the expandable portion thereof) may be adjusted according to the desired stent length. This may be accomplished by positioning a constraining member such as a sheath over the portion of the expandable member that is to remain unexpanded.

In one aspect, the stenting structure comprises a plurality of stent segments and adjusting the length of the deployable portion comprises repositioning a first stent segment relative to a second stent segment. In an exemplary embodiment, the stent segments are connected by separable couplings. Alternatively, the stent segments may be unconnected to each other. With such stent segments, the step of adjusting the length of the deployable portion may include constraining expansion of a selected stent segment by, e.g., a sheath.

The step of adjusting the length of the deployable portion may further include using a valve member on the catheter to separate the deployable portion from a remaining portion of the stenting structure. The valve member is disposed, in one embodiment, on a sheath slidably disposed over the stenting structure.

As mentioned previously, the stenting structure may be continuously connected through the length thereof. In these embodiments, the deployable portion of the stenting structure is separated from a remaining portion of the stenting structure at a selectable location on the stenting structure. The deployable portion may be severed from the remaining portion at the selectable location. Continuous stenting structures of the invention include coils and mesh structures, and are preferably self-expanding.

In yet another aspect of the invention, a method of deploying a stent of selectable length in a vessel comprises: endovascularly positioning a catheter in the vessel, the catheter having a distal end; deploying from the catheter a first stent having a first length; and deploying from the catheter a second stent having a second length different than the first length; wherein the first and second stents are deployed from the same location relative to the distal end of the catheter.

Further aspects of the nature and advantages of the invention will become apparent from the following detailed description taken in conjunction with the drawings.

BRIEF DESCRIPTION OF THE DRAWINGS

FIGS. 9A and 9C illustrate an alternative catheter construction intended for delivering self-expanding prostheses according to the methods of the present invention.

FIG. 11 illustrates an alternative catheter construction for delivering multiple prostheses via a heat-induction protocol in accordance with the principles of the present invention.

DETAILED DESCRIPTION OF THE SPECIFIC EMBODIMENTS

Figure 1:
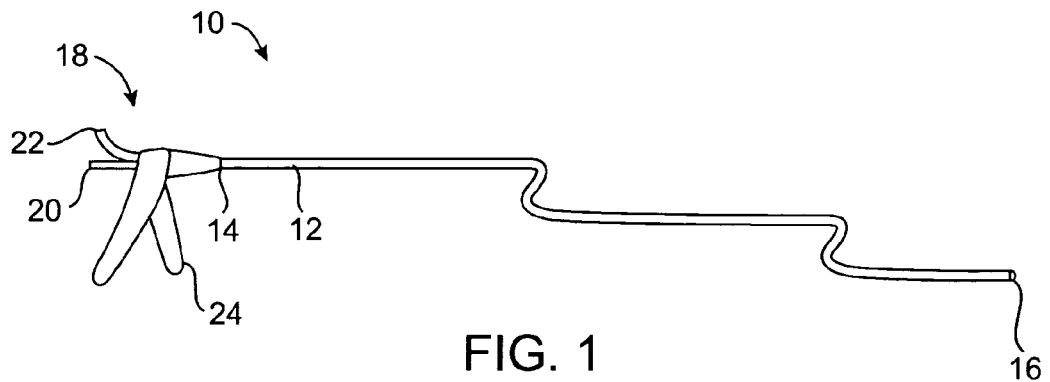
FIG. 1 is a perspective view illustrating a stent delivery catheter constructed in accordance with the principles of the present invention.

Referring now to FIG. 1, the stent delivery catheter 10 comprises a catheter body 12 having a proximal end 14 and a distal end 16. The catheter body is formed from a conventional catheter material, such as braided or coiled stainless steel, a natural or synthetic polymer, including silicone rubber, polyethylene, polyvinylchloride, polyurethane, polyester, polytetrafluoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French.

Figure 2:
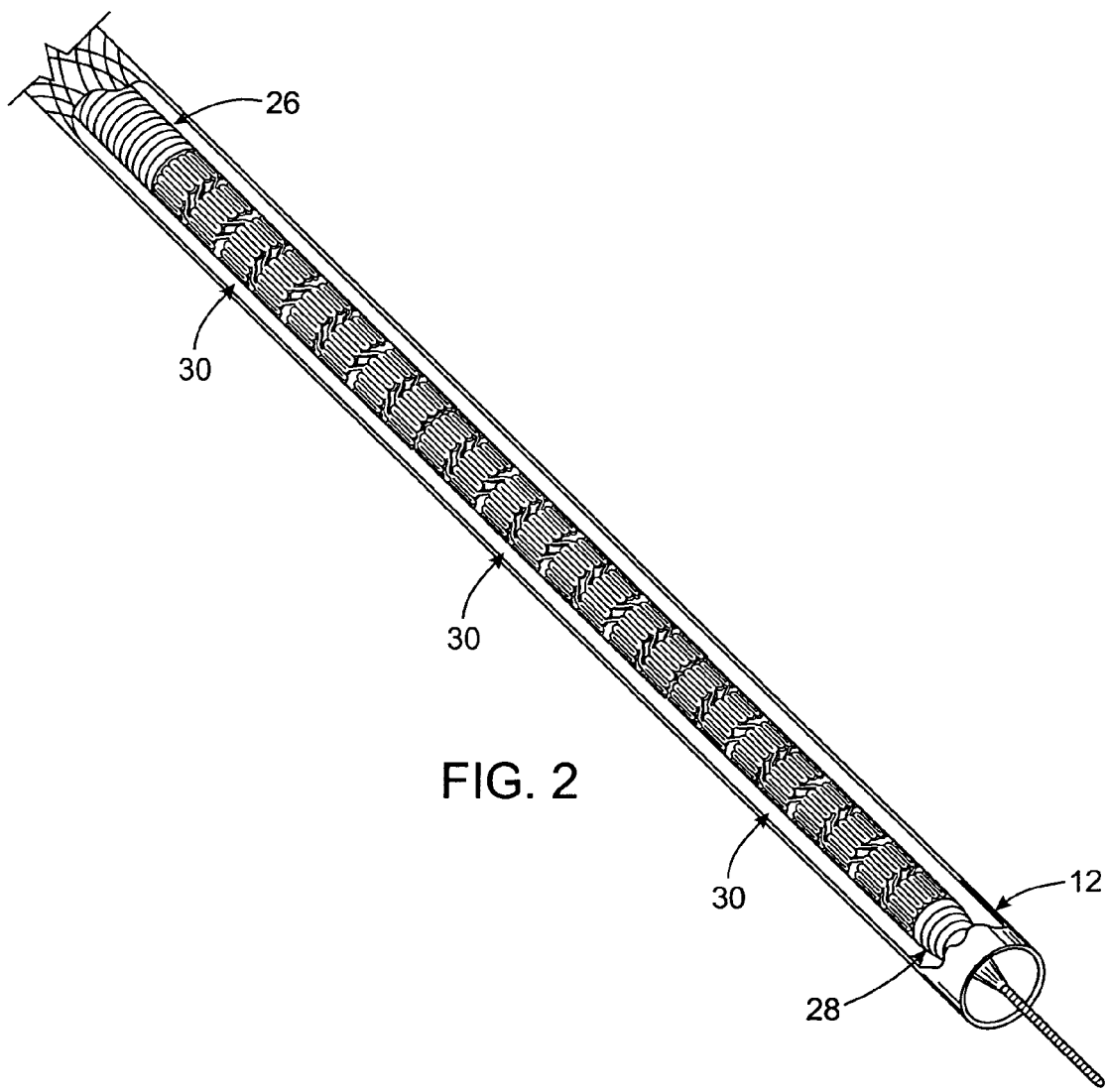
FIG. 2 is a detailed view of the distal end of the catheter of FIG. 1 with portions broken away.

Catheter 10 will include a handle 18 at its proximal end 14. The handle may include a guidewire port 20 and a balloon inflation port 22, as well as a handle grip 24 which advances a pusher shaft whose distal end 26 is shown in FIG. 2. Additionally, the handle permits reciprocation of a catheter delivery balloon 28, also shown in FIG. 2.

A plurality of stents 30 are carried in a lumen of the catheter body 12, as shown in FIG. 2. While three stents 30 are shown, it will be appreciated that additional stents may be carried generally within the ranges disclosed above. The illustrated stents comprise a plurality of serpentine ring structures joined by offset struts. It will be appreciated, however, that a wide variety of stent structures could be carried by the catheter 10, generally as described above.

Figure 3A:
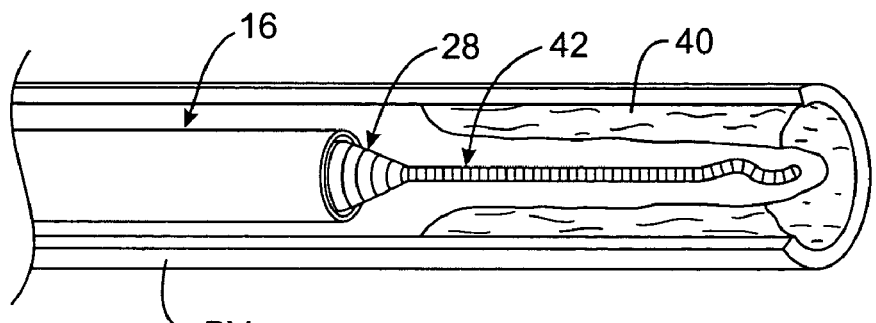
FIGS. 3A-3F illustrate use of the catheter of FIG. 1 for deploying a plurality of stents using balloon expansion.
Figure 3B:
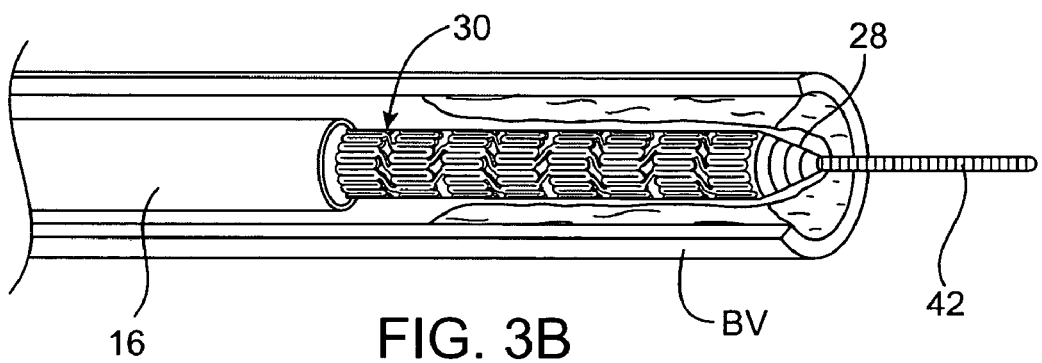
Figure 3C:
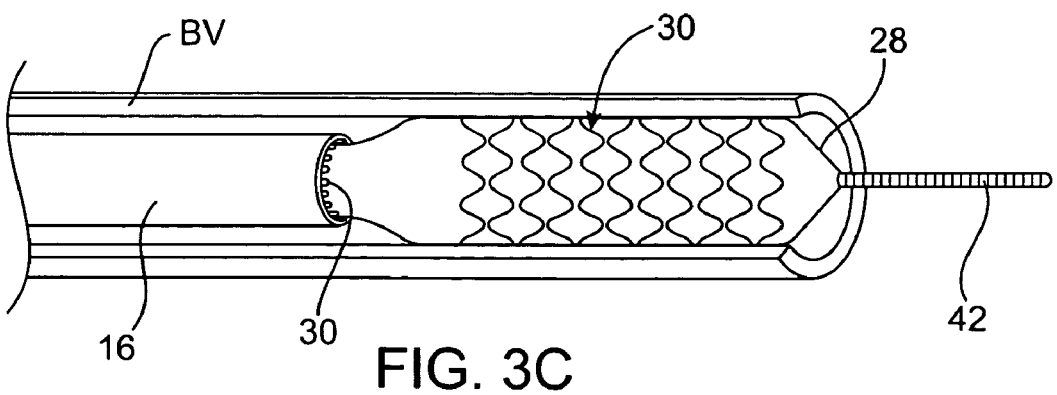

Referring now to FIGS. 3A-3F, the distal end 16 of the catheter 10 is advanced to target location 40 within a diseased blood vessel (BV) over a guidewire 42, as illustrated in FIG. 3B. Balloon 28 carries a first of the three stents 30, and is advanced distally from the catheter to deploy the stent within the treatment region 40, as illustrated in FIG. 3B (optionally by retracting the catheter body 12 proximally relative to balloon 28). Once the stent 30 is properly located, the balloon 28 is inflated to deploy the stent (and optionally dilate the treatment region), as illustrated in FIG. 3C.

Figure 3D:
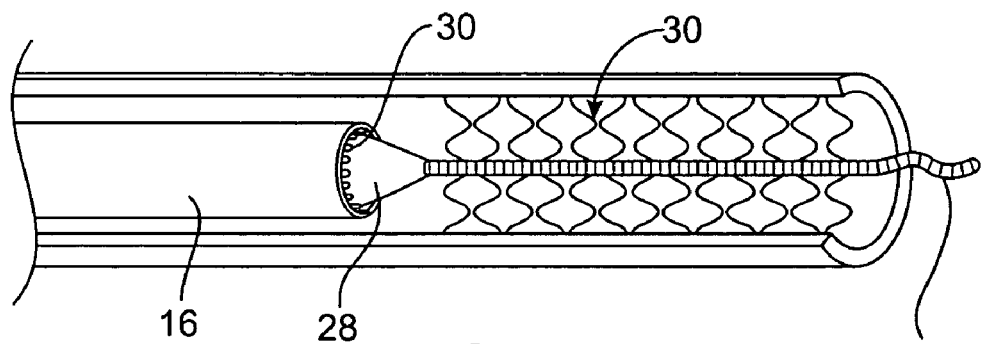
Figure 3E:
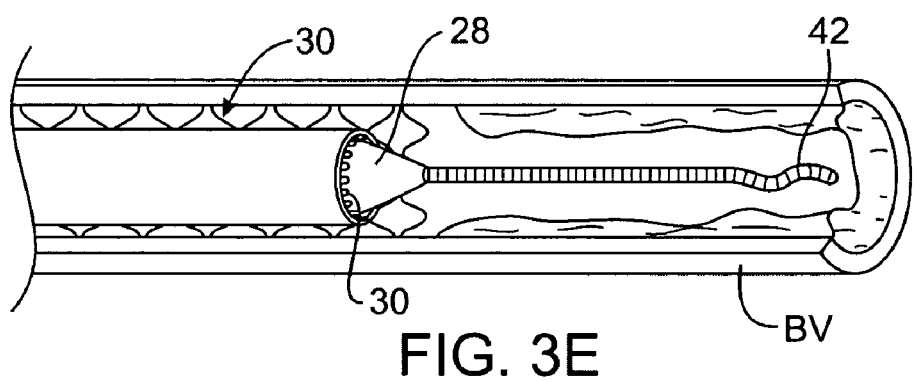
Figure 3F:
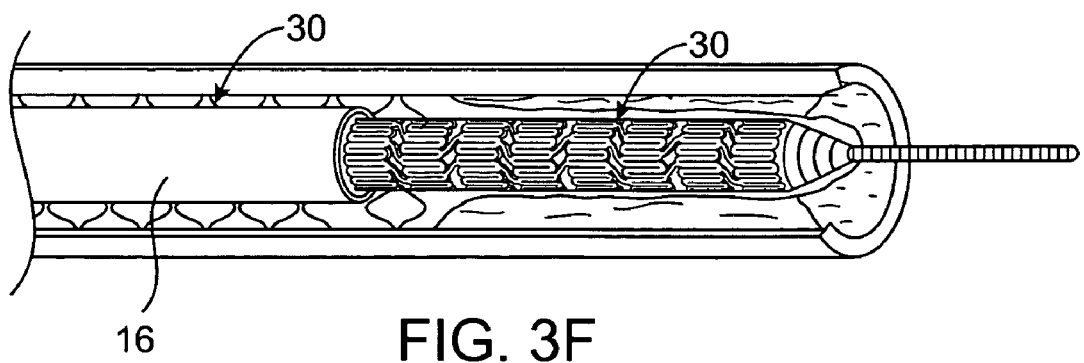

The balloon is then deflated, and retracted back into the distal end of the catheter 16, as illustrated in FIG. 3D. The expanded stent is left in place. The balloon 28 is retracted back to within the second stent 30, as illustrated in FIG. 3E. The second stent has been advanced using the pusher 26 so that it is properly located over the balloon 28, and the distal end of the catheter 16 may then be advanced so that the second stent 30 is located within a second treatment region spaced apart from the first treatment region. As illustrated in FIG. 3F, the treatment regions are adjacent to each other. It will be appreciated, however, that the second treatment region could be spaced a substantial distance from the first treatment region. Deployment of the second stent 30 is then completed in the same manner as described above for the first stent. Similarly, deployment of third, fourth, fifth, and additional stents 30 may be effected in the same manner. In this way, it will be appreciated that relatively lengthy and/or disseminated regions within a blood vessel may be treated.

Figure 4:
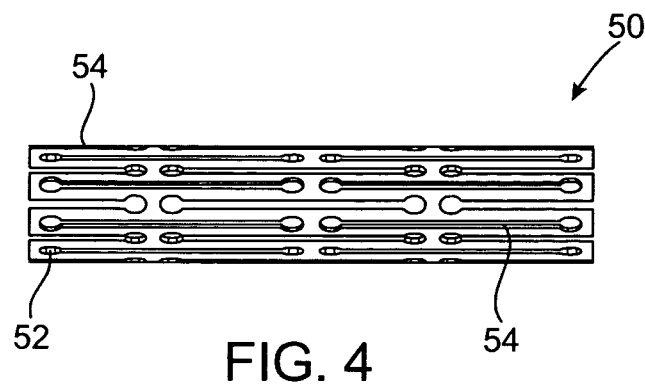
FIG. 4 illustrates an exemplary prosthesis constructed in accordance with the principles of the present invention.

Referring now to FIG. 4, an exemplary prosthesis 50 constructed in accordance with the principles of the present invention is illustrated. The prosthesis has a tubular body 52 having a plurality of axial slots 54, typically formed by laser cutting or chemical etching a tubular stock, such as stainless steel or nickel-titanium hypotube. Prosthesis 50, which may be delivered in groups of two, three, four, or more in accordance with the principles of the present invention, will have a length within the ranges set forth above. The diameter, prior to expansion, will typically be below 2 mm, preferably being below 1 mm, although in some instances much larger diameters can be used. The diameter of the prosthesis 50 upon expansion, of course, will be much greater, typically being at least twice as large, sometimes being at least three times as large, or even larger.

Figure 5A:
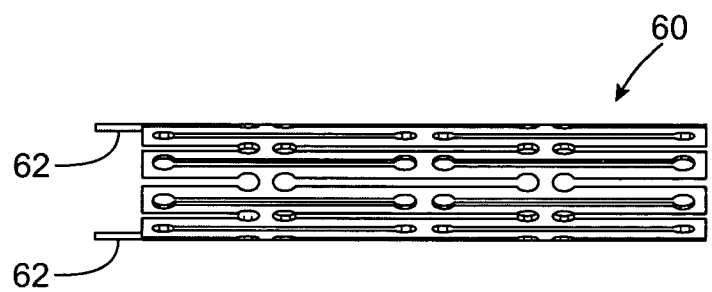
FIGS. 5A and 5B illustrate a prosthesis similar to that shown in FIG. 4, but further including coupling elements for permitting detachable coupling of adjacent prostheses.
Figure 5B:
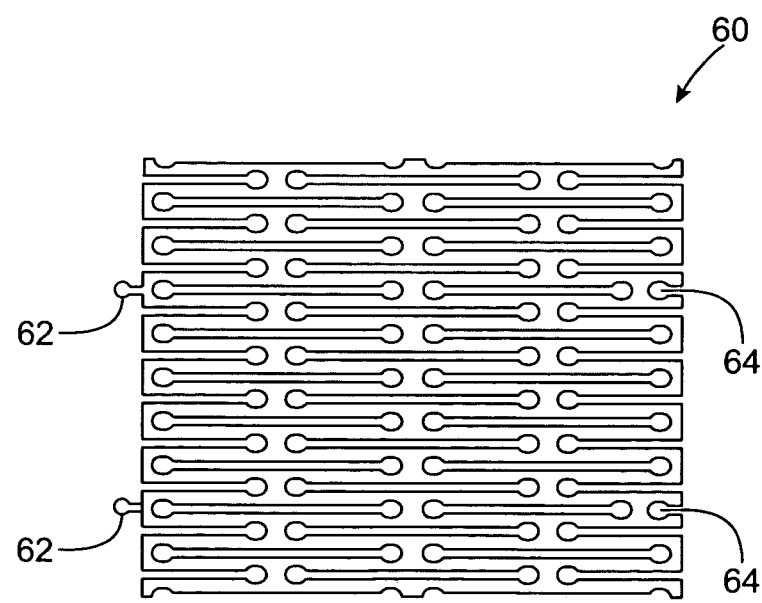

Referring now to FIGS. 5A and 5B, a prosthesis 60, similar to prosthesis 50, includes a pair of coupling elements 62 which are received in mating slots 64. FIG. 5B is a "rolled-out" view of the "rolled-out" view of the prosthesis 60 for better illustrating the coupling element 62 and slots 64 of the prosthesis 60.

Figure 5C:
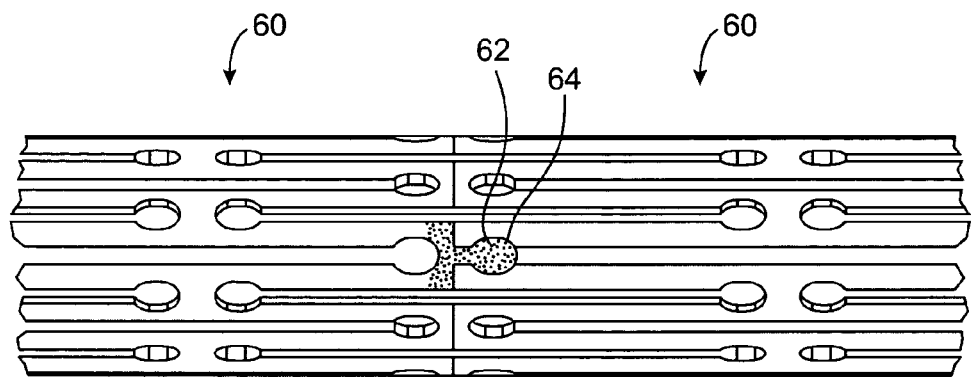
FIG. 5C illustrates a pair of prostheses, as shown in FIG. 5A and FIG. 5B, joined together by the coupling elements.

As shown in FIG. 5C, pairs of prosthesis 60 may be joined or coupled by circumferentially aligning the coupling element 62 with the slot 64. Although only a single coupling element 62 and slot 64 is visible in FIG. 5C, it will be appreciated that the second coupling element and slot will be located on the opposite side of the illustrated pair of prostheses.

Figure 5D:
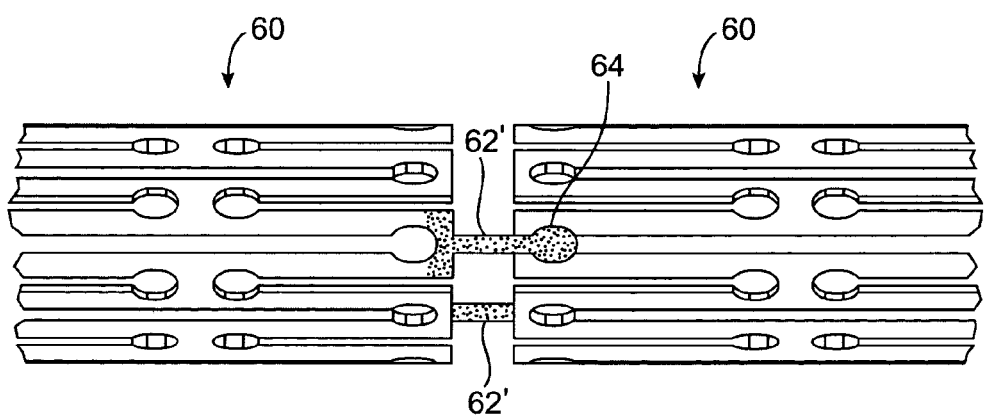
FIG. 5D illustrates a pair of adjacent prostheses coupled by a modified coupling element.

In FIG. 5C, the two prosthesis 60 are abutted directly against each other. Such a configuration is advantageous in that it provides for a substantially continuous stent or graft structure when the pair is expanded together in a body lumen. The structure, however, is disadvantageous in that it does not provide for flexibility at the point where the two prostheses meet. In order to provide for greater flexibility, as shown in FIG. 5D, a coupling element 62' can have an elongated shank to provide for a desired offset, typically in the range from 0.05 mm to 1 mm, preferably from 0.1 mm to 0.5 mm.

Figure 5E:
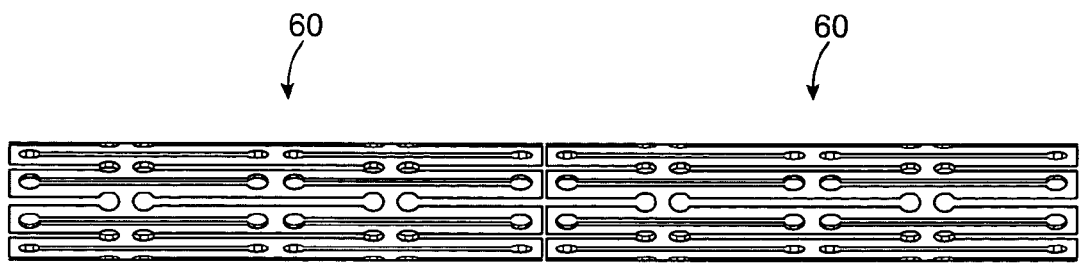
FIGS. 5E and 5F illustrate radial separation of the adjacent prostheses of FIG. 5C.
Figure 5F:
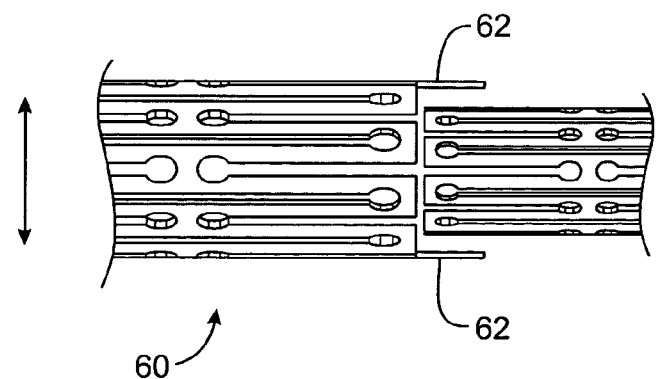

Referring now to FIGS. 5E and 5F, axial separation of the prostheses 60 is achieved by differential radial expansion of at least one of the prostheses. For example, when both prostheses 60 are in their unexpanded configurations, as shown in FIG. 5E, the coupling elements 62 are constrained by the slots 64, as previously described. By radially expanding the left-hand prostheses 60, as shown in FIG. 5F, the coupling elements 62 will be moved radially outwardly from the slots so that the two prostheses are no longer axially linked. It will be appreciated, however, that the two prostheses 60 may be radially expanded together (as described in more detail hereinafter) in a manner which preserves the link created by the coupling elements 62 and slots 64 so that combinations of two, three, four, or more prostheses may be delivered simultaneously and, in effect, provide a continuous prosthesis having a length which is some multiple of the length of each individual prostheses 60. The combined prostheses may then be separated from any additional prostheses (which remain in a delivery catheter as described below) by the radial expansion of those prostheses which are to be deployed. In this way, stents, grafts, or other prostheses may be delivered to the body lumen in both different lengths (by properly selecting the number of individual prostheses 60) and at different locations (by releasing individual or multiple prostheses 60 at different portions of the body lumen).

Figure 6A:
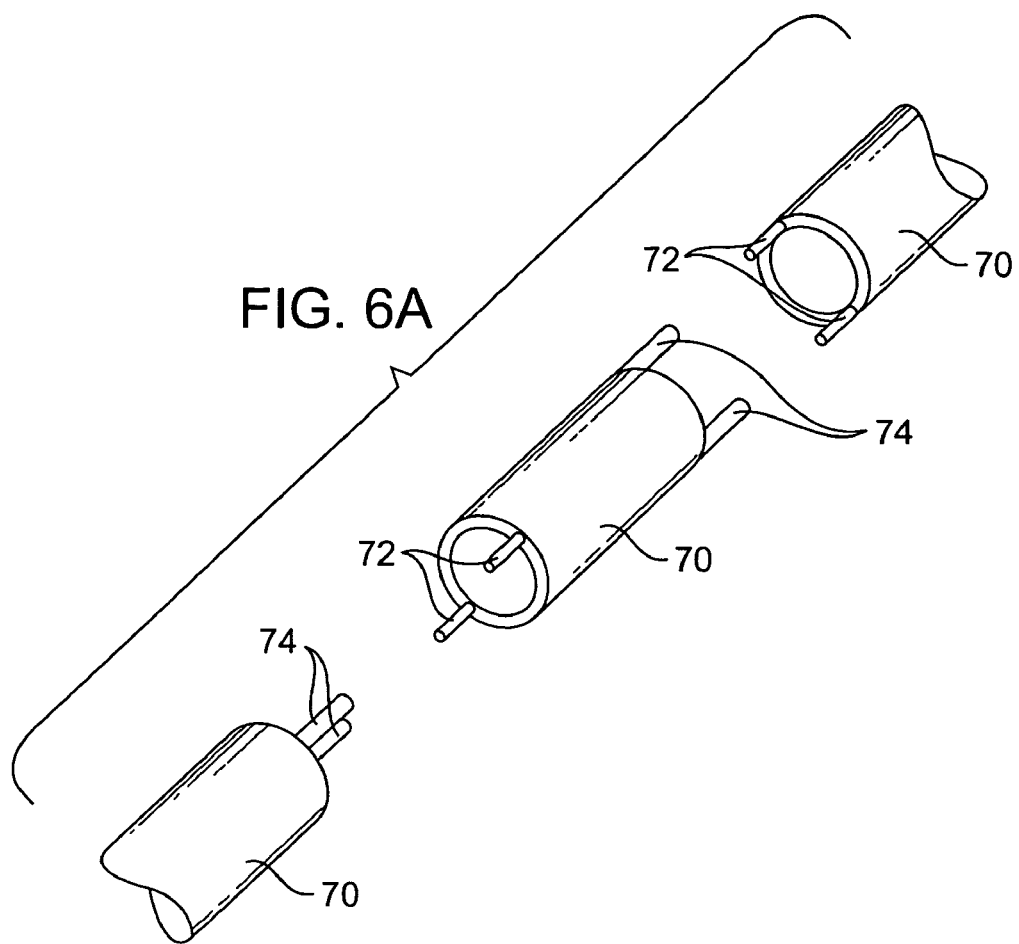
FIGS. 6A and 6B illustrate a second coupling mechanism constructed in accordance with the principles of the present invention.
Figure 6B:
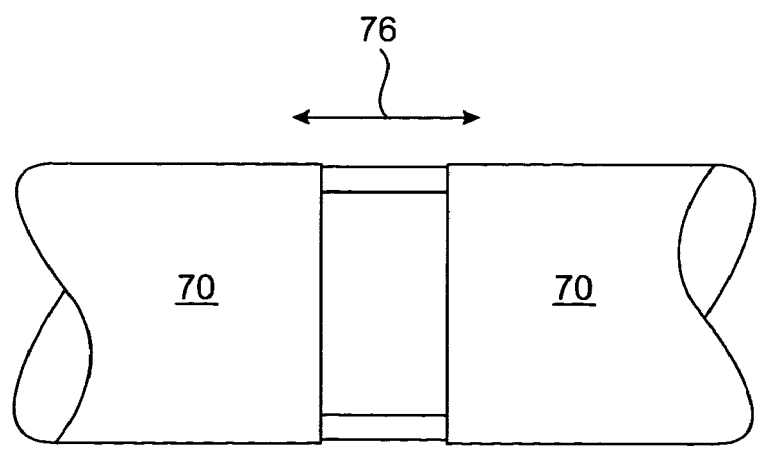

Axially separable coupling elements may also be provided, as illustrated in FIGS. 6A and 6B. Each prosthesis 70 includes a pair of male coupling elements 72 at one end and a pair of female coupling elements 74 at the other end. The male coupling elements 72 are typically short rods which extend axially from the periphery of the prosthesis and the female coupling elements are typically short tubes having hollow interiors which detachably receive the male coupling elements. Thus, the prostheses 70 may be joined in an end-to-end manner, as shown in FIG. 6B. The prostheses are separated by pulling them in an axial direction, as shown by arrow 76, but will remain linked under axial compression as well as when exposed to a substantial bending moment. Thus, the axially separable coupling structures of FIGS. 6A and 6B are advantageous in that they remain linked during deployment of the prostheses 70, even when deployment involves significant bending and radial stress. Separation may be effected by pullback on the delivery catheter in order to disengage the coupling elements 72 and 74.

Figure 7:
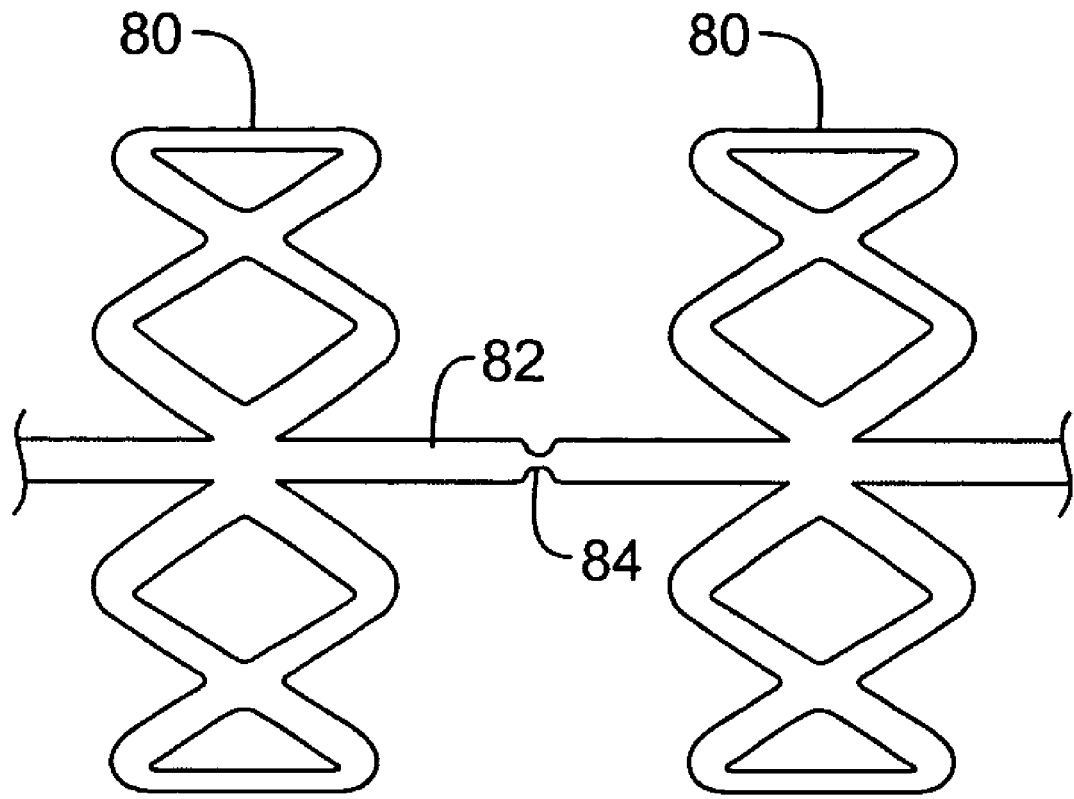
FIG. 7 illustrates a frangible linkage for joining a pair of adjacent prostheses.

A third approach for detachably coupling adjacent prostheses 80 is illustrated in FIG. 7. Each prosthesis 80 comprises an expansible ring of diamond-shaped members. Other conventional stent or prostheses structures, however, could also be used. The adjacent prostheses 80 are joined by an axial beam 82 which preferably includes a weakened segment 84 near its midpoint. The use of such a joining structure, which will require physical breakage (as opposed to the simple detachment characteristic of the embodiment of FIGS. 5 and 6) is advantageous in that it provides a very strong linkage which permits both the application of axial compression and axial tension without decoupling. The disadvantage of such a linkage is that it usually requires some mechanism or capability to be incorporated in the delivery catheter to permit selective breakage of the couple.

Figure 8A:
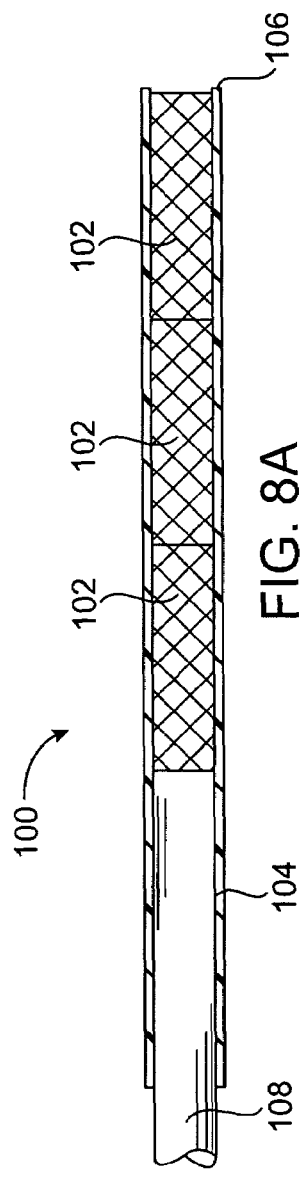
FIGS. 8A-8C illustrate a catheter and its use for delivering self-expanding prostheses according to the methods of the present invention.
Figure 8B:
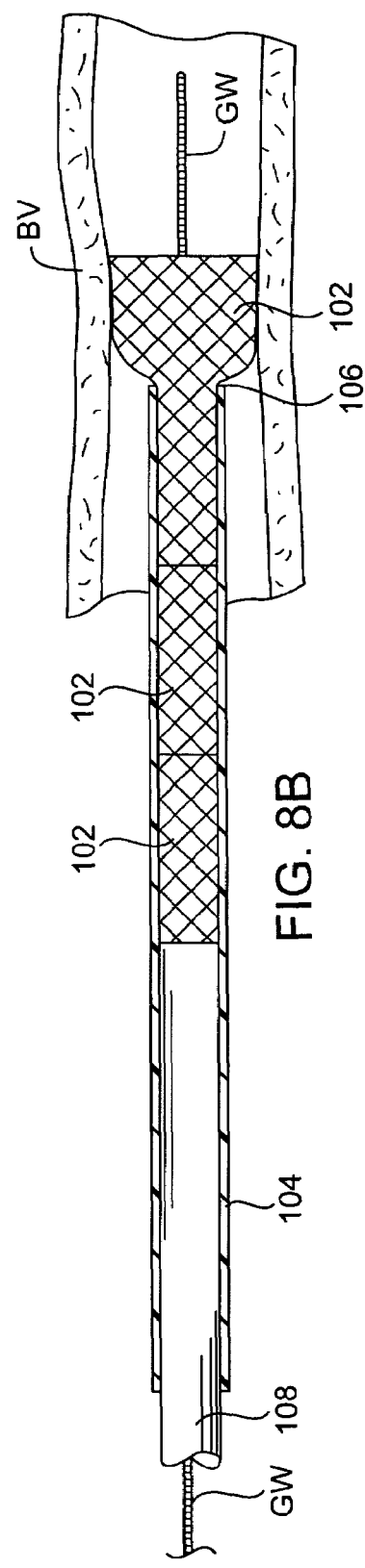
Figure 8C:
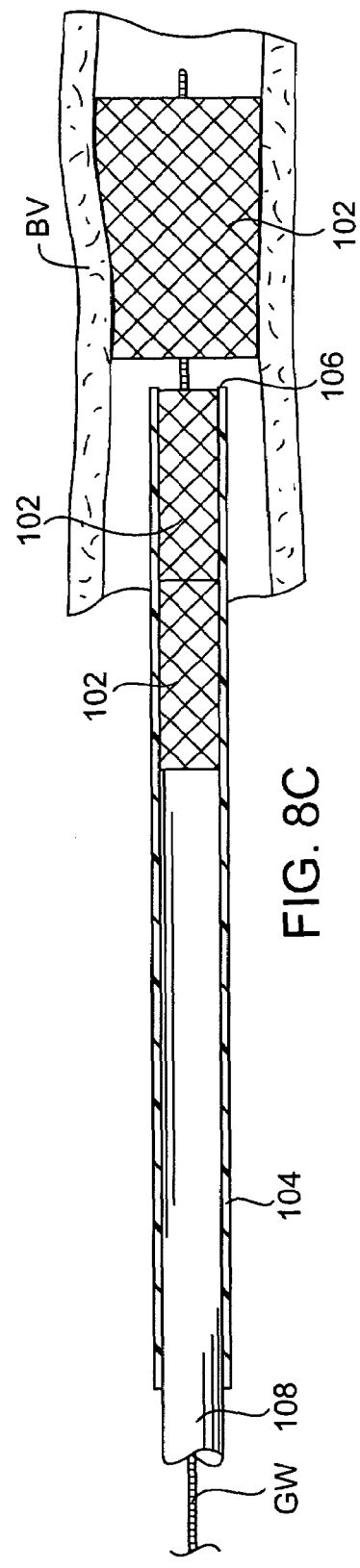

Referring now to FIGS. 8A-8C, a catheter 100 suitable for delivering a plurality of self-expanding prostheses 102 will be described. Catheter 100 comprises a sheath 104 having an axial lumen which carries the prostheses 102 near its distal end 106. A pusher tube 108 is also positioned in the lumen and is located proximally of the proximal most prosthesis 102. The individual prostheses 102 may be delivered into a body lumen, typically a blood vessel BV, as illustrated in FIG. 8B. The catheter is introduced over a guidewire GW to a desired target site in the blood vessel BV. When at the target site, a first of the prostheses 102 is deployed by axially advancing the pusher tube 104 so that the line of prostheses 102 is axially advanced, with the distal-most prostheses 102 being released from the distal end 106 of the catheter. As it is released, the distal-most prostheses 102 expands since it is being released from the radial constraint provided by the sheath 104.

Figure 9C:
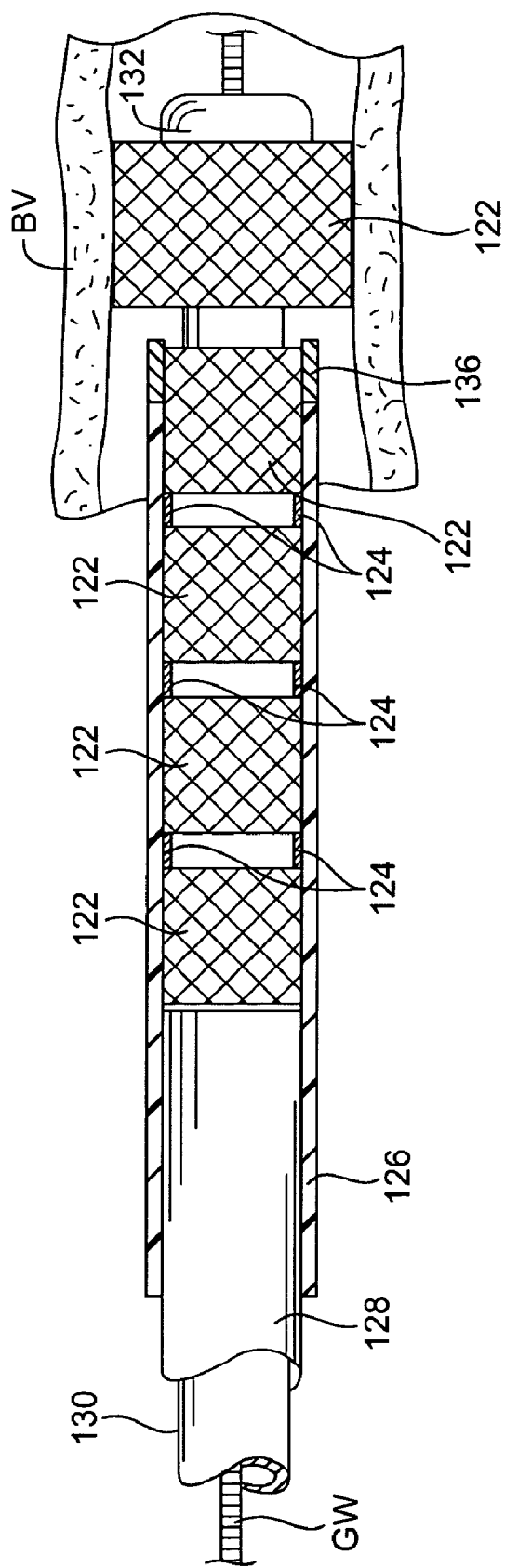

Catheter 100 of FIGS. 8A-8C is intended for delivering prostheses which abut each other in an end-to-end manner, but which are otherwise unconnected. A catheter 120 intended for releasing self-expanding prostheses 122 which are mechanically linked by frangible coupling elements 124 is illustrated in FIGS. 9A-9C. The prostheses 122 and coupling elements 124 may be similar to the prosthesis structure shown in FIG. 7, or may comprise other linked prosthesis or stent structures, for example as shown in U.S. Pat. No. 6,258,117, the disclosure of which is incorporated herein by reference.

Catheter 120 comprises a sheath 126, a pusher tube 128, and a catheter body 130 having a shearing element 132 at its distal end. Conveniently, the pusher tube 128 is coaxially received over a shaft 134 of the catheter body 130. In this way, the pusher tube may be used to axially advance each prosthesis 122 by pushing on the proximal end of the proximal-most prosthesis, as shown in FIG. 9B.

The catheter 120 is advanced over a guidewire GW to a desired target site in a blood vessel BV. After reaching the target site, at least a first prosthesis 122 is advanced from the distal end of the sheath so that it radially expands to engage an inner wall of the blood vessel. After the at least one prosthesis 122 is advanced sufficiently far, the frangible coupling elements 124 will reach a shearing element 136, typically a metal ring, disposed at the distal end of the sheath 126. By then axially retracting the catheter body 130, a chamfered surface 138 of the shearing element 132 is engaged against the shearing element 136 in order to shear the links 122, releasing the prosthesis 122, as illustrated in FIG. 9C. After deployment and release of the first prosthesis 122, additional prosthesis 122 may be released adjacent to the first prosthesis or at different, axially spaced-apart locations within the blood vessel.

Figure 10A:
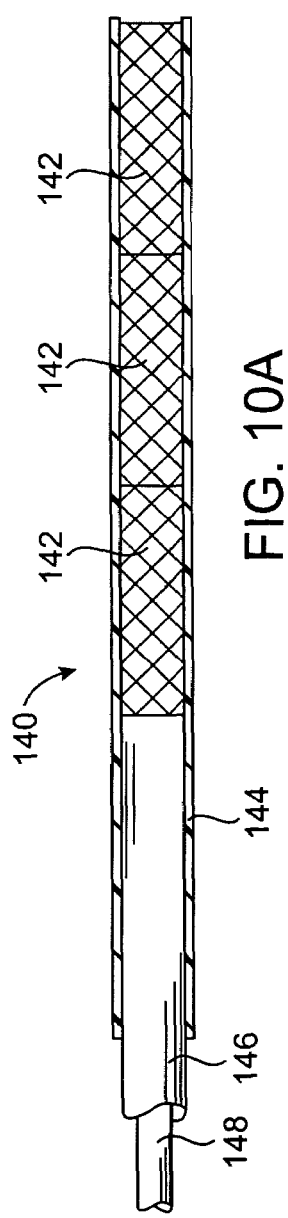
FIGS. 10A-10C illustrates use of the catheter for delivering prostheses by a heat-induction method in accordance with the principles of the present invention.
Figure 10B:
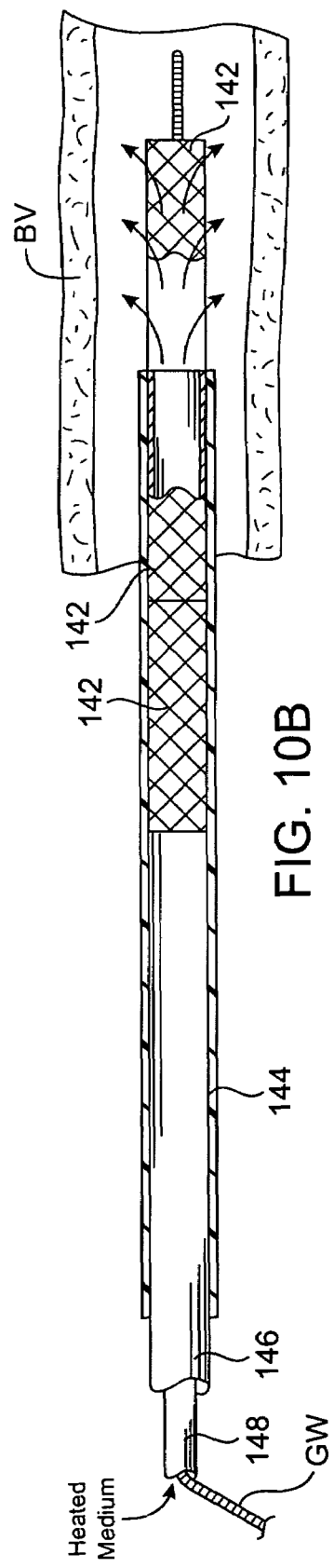
Figure 10C:
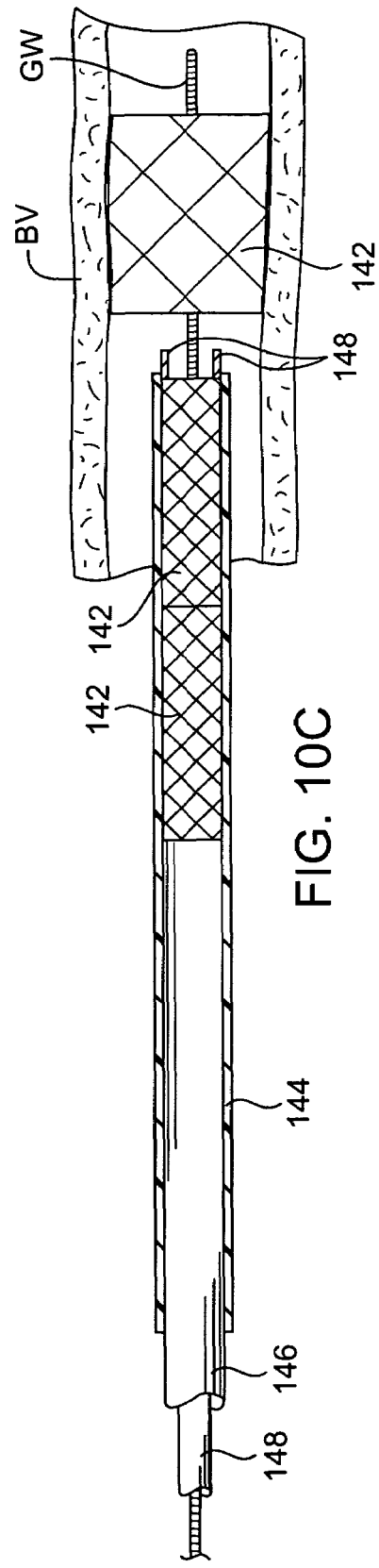

Referring now to FIGS. 10A-10C, a catheter 140 for delivering a plurality of heat expansible prostheses 142 is illustrated. The prostheses 142 are composed of a heat memory alloy, such as a nickel titanium alloy, which has been programmed to remain in an unexpanded configuration when maintained at body temperature or below, and to assume an expanded configuration when exposed to temperatures above body temperature, typically temperatures above 43° C., often above 45° C. The prostheses will have coupling members which anchor successive prostheses 142 together, typically the radially separating anchors illustrated in FIGS. 5A-5F.

The catheter 140 includes a sheath 144 and a pusher tube 146. The catheter 140 is advanced to a desired target site within the blood vessel BV over a guidewire GW in a conventional manner. After the distal-most prostheses 142 has been fully advanced from the sheath 144 (usually by retracting the sheath 144 while the prostheses are held stationary relative to the blood vessel BV using the pusher tube 146), as shown in FIG. 10B, it will remain both unexpanded and attached to the next proximal prosthesis 142 which remains within the sheath. It is important that the advanced prosthesis 142 be anchored or tethered to the remaining prostheses since it has not yet been expanded and it would otherwise be lost into the lumen of the blood vessel.

After the uncovered prostheses is properly positioned, a heated medium may be introduced through a lumen of the catheter body 148 so that it flows outwardly through the interior of the distal-most prosthesis 142. By properly selecting the temperature of the heated medium, the prosthesis to be deployed can be heated sufficiently to induce radial expansion, as illustrated in FIG. 1C. By positioning the catheter body 148 so that its distal tip is coterminous with the distal tip of the sheath 144, inadvertent heating of the prostheses 142 which remain within the sheath can be avoided. After the prosthesis 142 has radially expanded, it will separate from the coupling elements 148 located on the next prosthesis which remains within the sheath 144. Additional ones or groups of prostheses 142 may then be deployed, either at the same target site or at a different target site axially spaced-apart within the lumen of the blood vessel BV.

As illustrated in FIG. 11, instead of using an internal catheter body 148, as illustrated in FIGS. 10A-10C, an external sheath 150 may be used to deliver the heated medium around one or more deployed prostheses 142. Other aspects of the construction of catheter 140 may remain the same. Optionally, if prosthesis is martensitic at body temperature, further radial expansion can be achieved by internal balloon expansion.

Figure 12A:
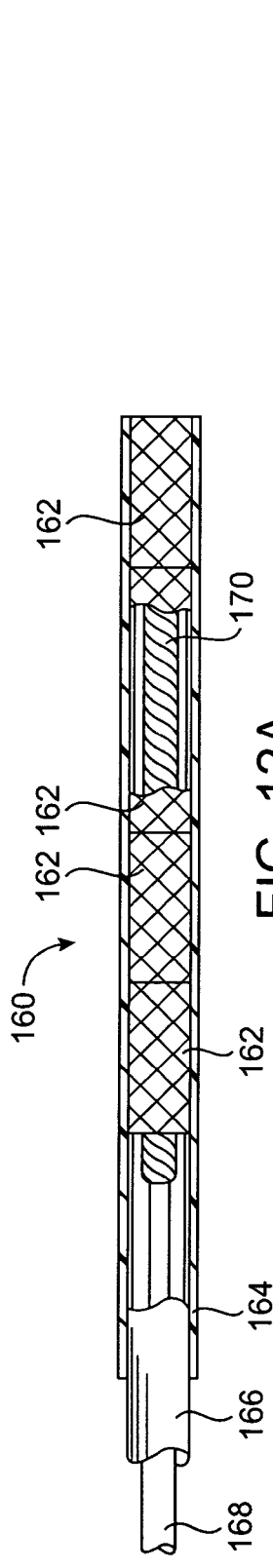
FIGS. 12A-12D illustrate a catheter for delivering multiple prostheses using balloon expansion in accordance with the methods of the present invention.
Figure 12B:
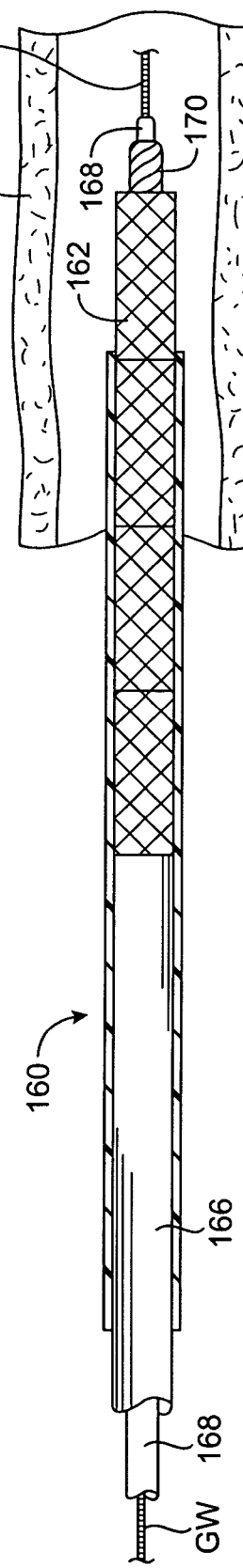
Figure 12C:
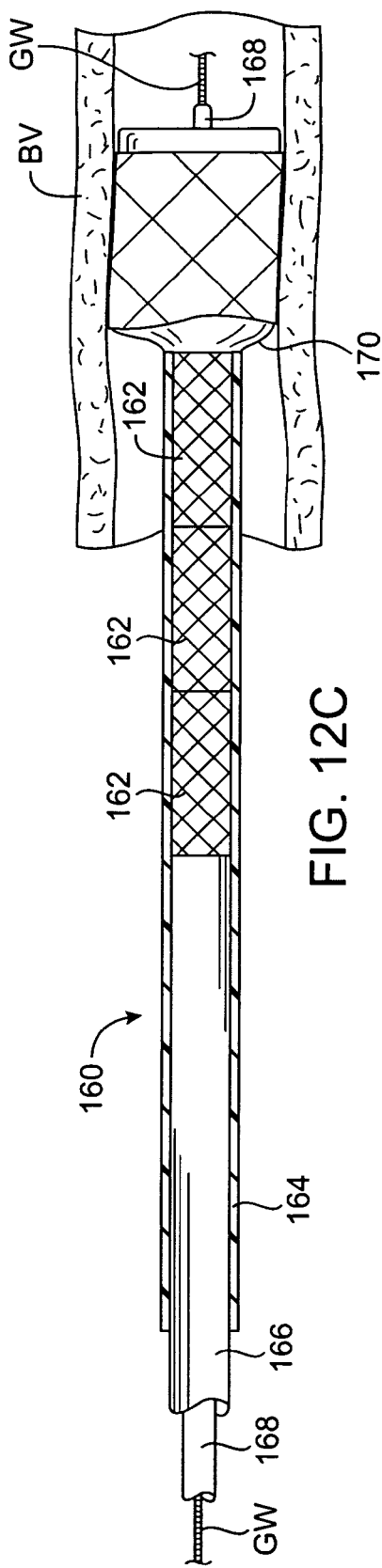

Referring now to FIGS. 12A-12D, catheter 160 intended for delivery of multiple prostheses 162 by balloon deployment is illustrated. Catheter 160 comprises a sheath 164, pusher tube 166, and a catheter body 168. The catheter body 168 includes an expansible balloon 170 over its distal portion. Individual prostheses 162 are deployed, as illustrated in FIGS. 12B and 12C, by crossing the target area with catheter 160 and then retracting sheath 164. A distal portion of the balloon 170 lies within the distal-most deployed prosthesis 162, as shown in FIG. 12B. The remaining proximal portion of the balloon 170 will, of course, remain within the other prostheses 162 which themselves remain within the sheath 164. The balloon 170 is then inflated, but only the distal portion of the balloon beyond the sheath inflates within the distal prosthesis 162, as illustrated in FIG. 12C. Expansion of the remaining proximal portion of the balloon is prevented by the sheath 164. Similarly, the remaining prostheses 162 remain unexpanded since they remain within the sheath 164. After deployment of prostheses 162, balloon 170 may be deflated and retracted into sheath 164 and remaining prostheses 162.

Figure 12D:
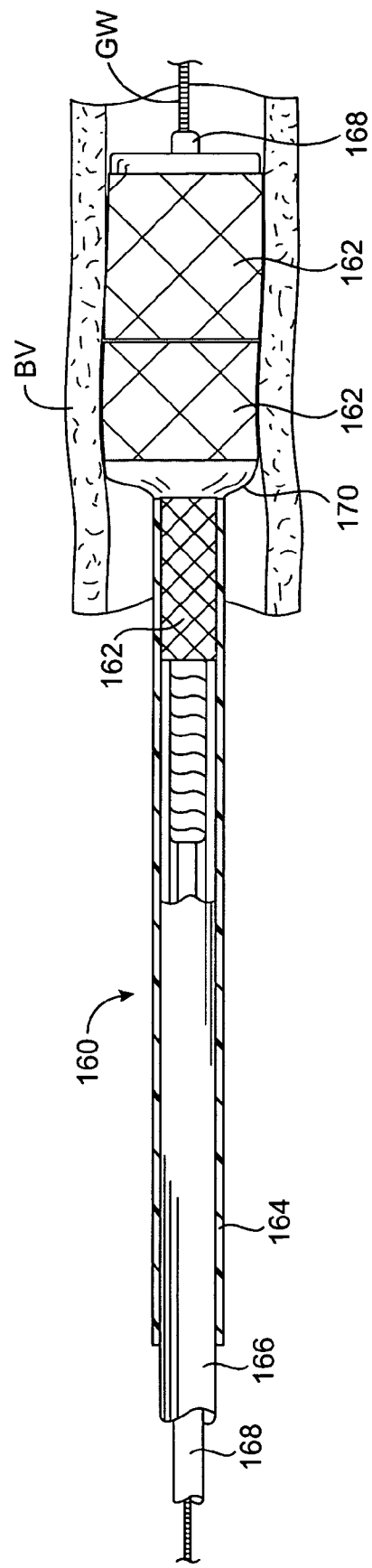

Referring now to FIG. 12D, additional prostheses 162 may be deployed, either at the same target location within the blood vessel or at a different, spaced-apart locations within the blood vessel. Deployment of two prostheses 162 is illustrated. The two prostheses 162 are axially exposed as the sheath is retracted over the stents which are positioned over the uninflated balloon 170. The balloon 170 is then inflated, as illustrated in FIG. 12D, thus expanding the prostheses 162 within the blood vessel BV. It will be appreciated that the catheter 160 could carry many more than the four illustrated prostheses 162, and three, four, five, ten, and even 20 or more individual prostheses could be deployed at one time, with additional single prostheses or groups of prostheses being deployed at different times and/or at different locations within the blood vessel.

Figure 13A:
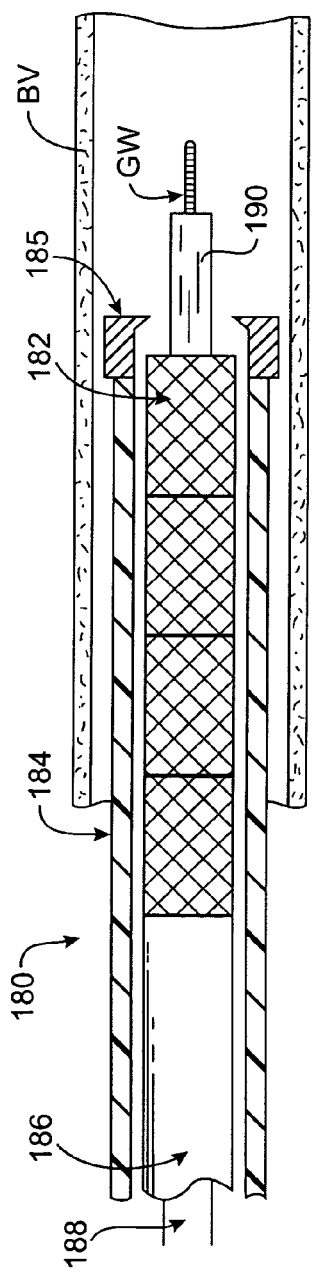
FIGS. 13A-13D illustrate a catheter including a stent valve for delivering multiple prostheses using balloon expansion in accordance with the methods of the present invention.
Figure 13B:
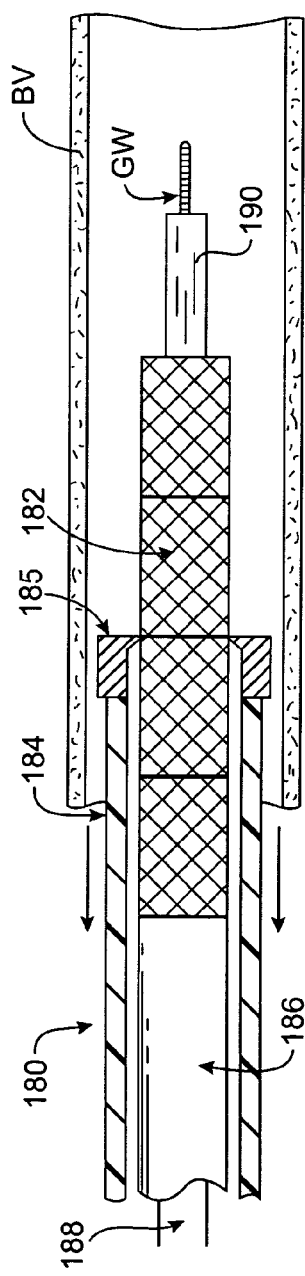
Figure 13C:
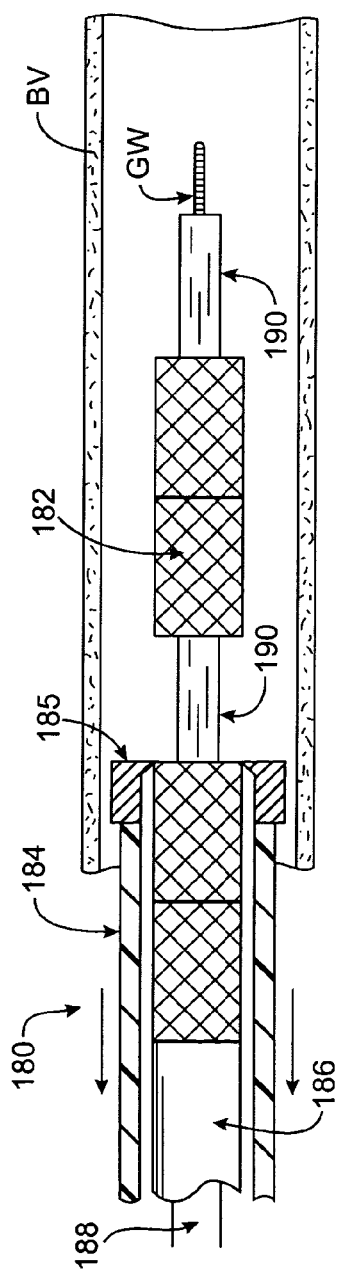
Figure 13D:
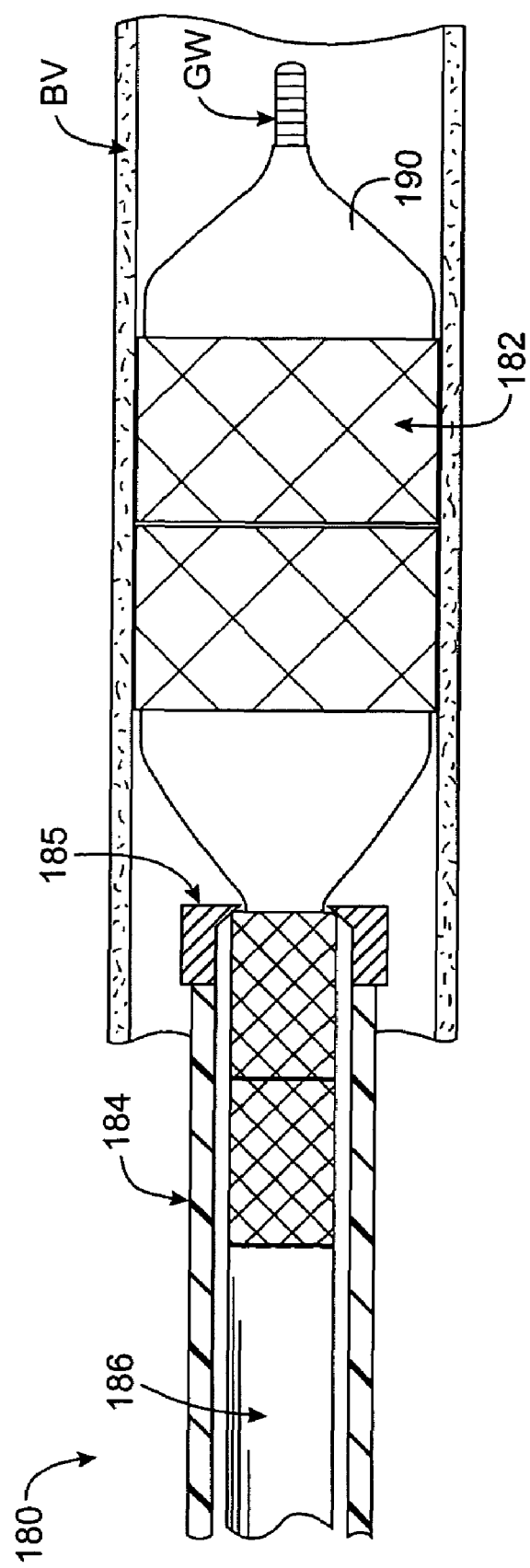

Referring now to FIGS. 13A-13D, another embodiment of a catheter 180 intended for delivery of multiple prostheses 182 by balloon deployment is illustrated. In this embodiment, catheter 180 comprises a sheath 184 having a valve member 185 at its distal end, a pusher tube 186, and a catheter body 188. The catheter body 188 includes an expansible balloon 190 over its distal portion. To deploy prostheses 182, as illustrated in FIG. 13B, a predetermined number of prostheses 182 is first exposed by retracting sheath 184 proximally (arrows) while holding pusher tube 186 in place. As shown in FIGS. 13B and 13C, valve member 185 may be used to engage a distal end of one of the prostheses 182 and the sheath 184 and the pusher tube may be retracted proximally together (arrows in FIG. 13C) to separate a proximal number of prostheses 182 from a distal number of prostheses 182. The distal portion of the balloon 190 lies within the distal, deployed prostheses 182. The remaining proximal portion of the balloon 190 will remain within the other prostheses 182 which themselves remain within the sheath 184. The balloon 190 is then inflated, as shown in FIG. 13D, but only the distal portion of the balloon inflates within the distal prostheses 182, as illustrated in FIG. 12C. Expansion of the remaining proximal portion of the balloon is prevented by the sheath 184. Similarly, the remaining prostheses 182 remain unexpanded since they remain within the sheath 184.

Referring now to FIG. 13D, single or multiple prostheses 182 may be deployed at the same target location within the blood vessel. Additional prostheses 182 may also be deployed at different, spaced-apart locations within the blood vessel. Deployment of two prostheses 182 is illustrated at one location in FIG. 13D. It will be appreciated that the catheter 180 could carry many more than the four illustrated prostheses 182, and three, four, five, ten, and even 20 or more individual prostheses could be deployed at one time, with additional single prostheses or groups of prostheses being deployed at different times and/or at different locations within the blood vessel.

Figure 14:
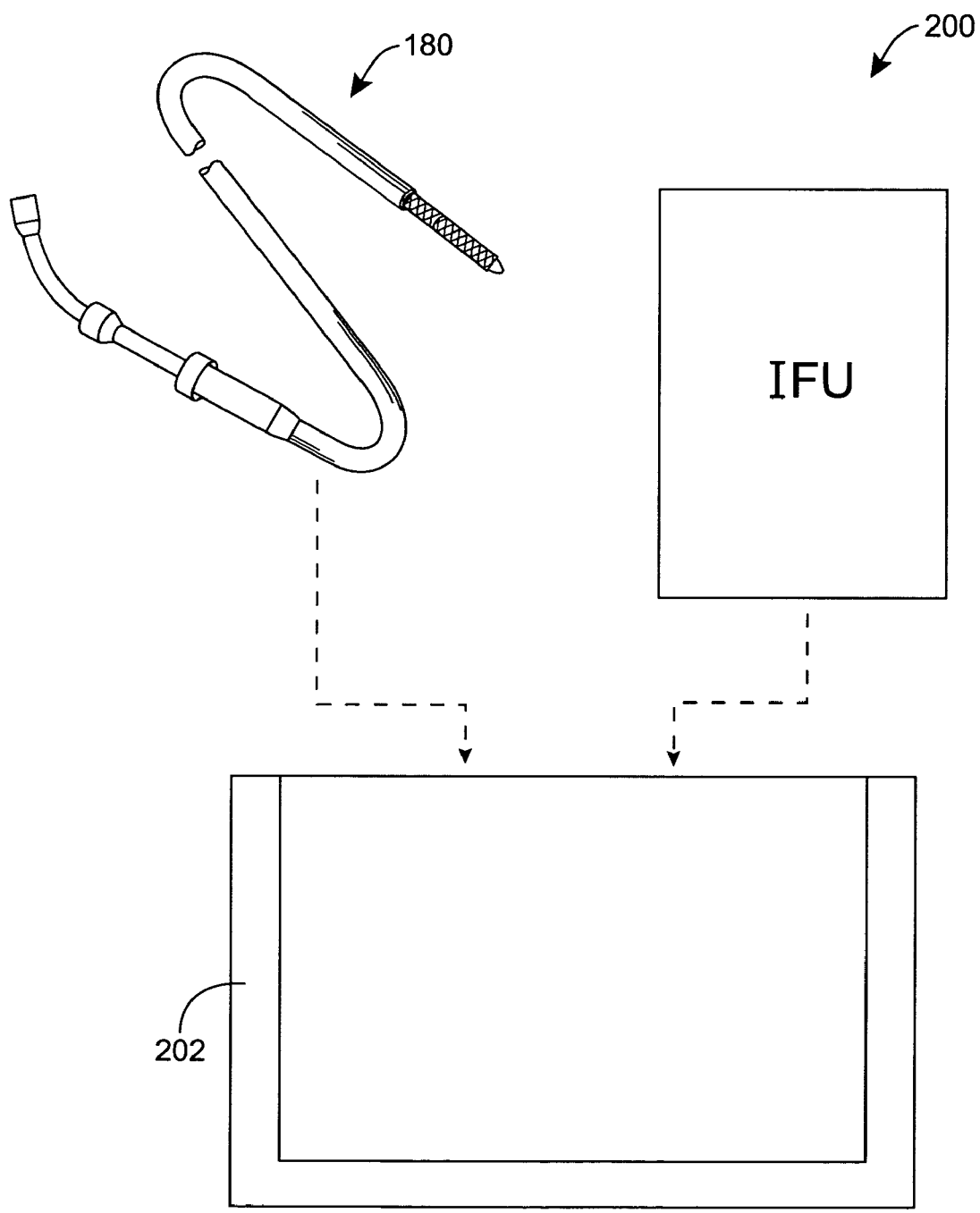
FIG. 14 illustrates an exemplary kit constructed in accordance with the principles of the present invention.

Referring now to FIG. 14, kits 200 according to the present invention comprise a catheter 160 (or any other of the illustrated catheters of the present invention) in combination with instructions for use IFU. The instructions for use set forth any of the methods of the present invention, and in particular set forth how the catheter 180 may be used to implant single or multiple prostheses within a blood vessel or other body lumen. The catheter 180 and instructions for use will typically be packaged together, for example within a conventional package 202, such as a box, tube, pouch, tray, or the like. Catheter 160 will typically be maintained in a sterile condition within the package 202. The instructions for use may be provided on a package insert, may be printed in whole or in part on the packaging, or may be provided in other ways, such as electronically over the internet, on an electronic medium, such as a CD, DVD, or the like.

Figure 15:
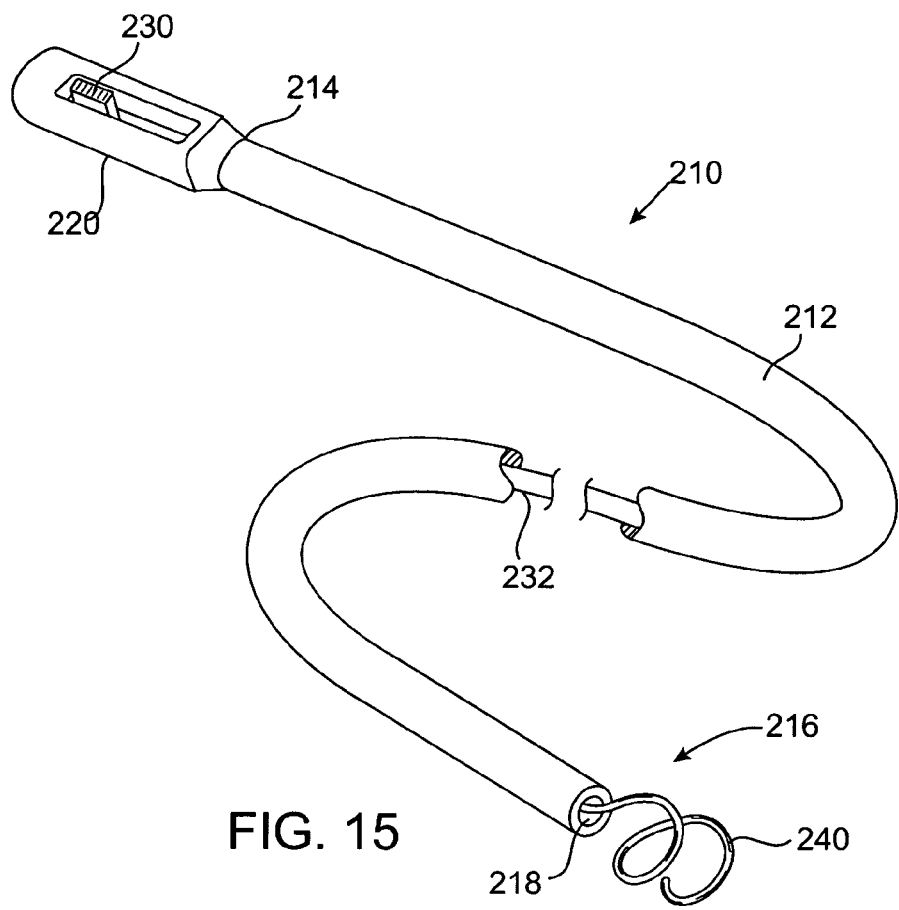
FIG. 15 is a perspective view of a catheter capable of delivering helical elements constructed in accordance with the principles of the present invention.

Referring to FIG. 15, a delivery device comprising a catheter 210 includes a catheter body 212 having a proximal end 214 and a distal end 216. The catheter will include at least one lumen 218 (FIG. 16) extending over at least a portion thereof, and will further include a proximal hub 220 attached to the proximal end 214. Hub 214 will include a mechanism for advancing a linearized element 226 from the lumen 218, such as a thumb slide 230. In the exemplary embodiment, the thumb slide will be attached to a push rod 232 which extends through the lumen 218 and engages the linearized element(s) 240 to be advanced from the catheter. As shown in FIG. 15, the linearized element 240 assumes a helical non-linear configuration as it is advanced from the lumen 218 of the catheter body 212.

Figure 16:
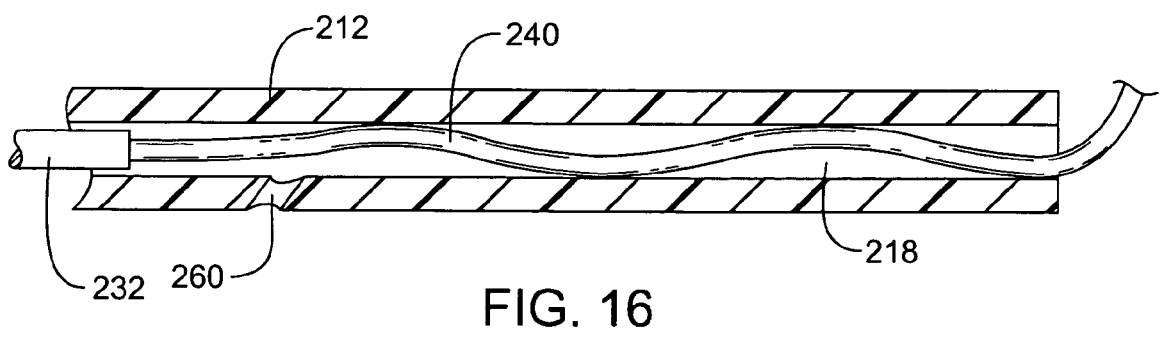
FIG. 16 is a detailed view of the distal end of the catheter of FIG. 15, shown in section.
Figure 15A:
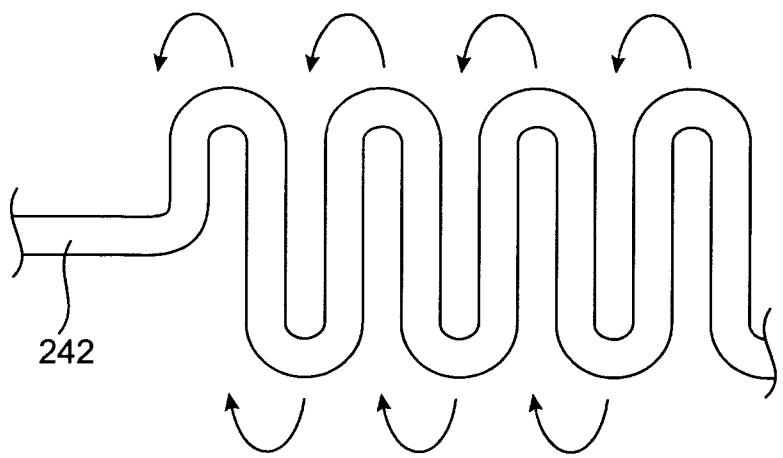
FIGS. 15A and 15B illustrate alternatively non-linearized element geometries according to the present invention.
Figure 15B:
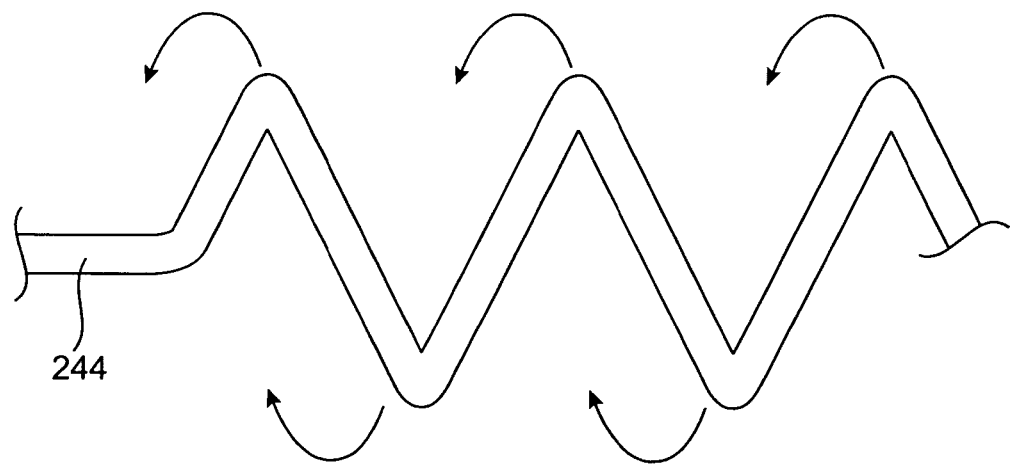

Referring now to FIG. 15A, an alternative linearized element 242 is illustrated which will assume a serpentine non-linear configuration when advanced from the catheter or other delivery device. FIG. 15A shows the serpentine structure in its flattened or "rolled-out" configuration. It will be appreciated that the scaffold provided by the serpentine structure will be rolled into a generally tubular configuration, as indicated by the arrows in FIG. 15A. When linearized, the element 242 will still assume a generally straight configuration, as shown in FIG. 16. A second alternative non-linear geometry comprises the zigzag pattern shown in FIG. 15B. Again, FIG. 15B illustrates this pattern in its flattened or rolled-out configuration. The actual device would be rolled as indicated by the arrows into a generally tubular configuration to serve as a scaffold structure in the present invention.

As illustrated in FIG. 16, a single linearized element 240 is pushed by the pusher rod 232 to assume its helical or rather non-linear configuration when fully released from the catheter body 212. Since the linearized element 240 and the pusher rod 242 are not connected, there is no need to provide a severing or other release mechanism in the embodiment of FIG. 16.

Figure 17:
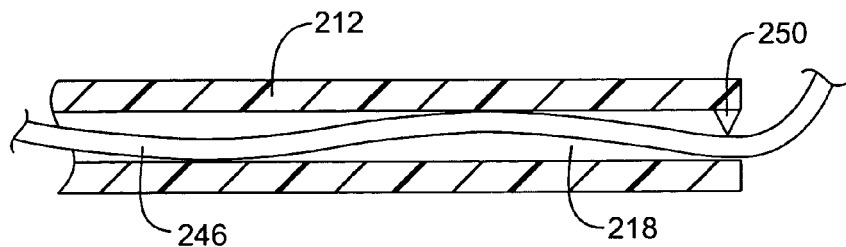
FIG. 17 is an alternative view of the distal end of the catheter of FIG. 15, shown in section.

FIG. 17, in contrast, shows a linearized element 246 having an indeterminate length. That is, the linearized element 246 will be sufficiently long so that it may be divided into two, three, four, or an even larger number of discrete non-linearized elements upon release from the catheter body 212. In order to effect such release, a severing device 250, such as an actuable blade, electrochemical, or other severing mechanism, is provided at the distal end of the delivery device. In this way, once a non-linear structure having a sufficient length has been delivered, the transition point between the linearized element and the non-linearized element will be severed using the device 250. Additional non-linear scaffold devices may then be delivered using the same catheter over regions space-part within the vasculature or other body lumens.

Figure 18:
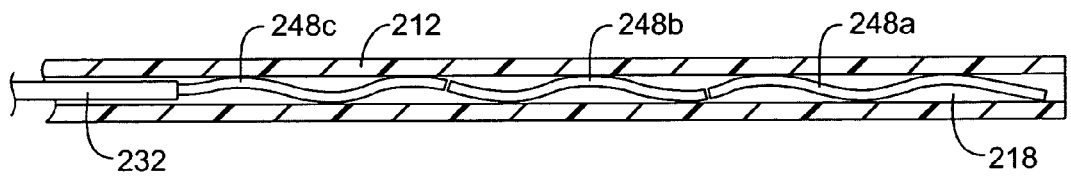
FIG. 18 is a second alternative view of the distal end of the catheter of FIG. 15, shown in section.

Referring now to FIG. 18, a third alternative advancement and release mechanism is illustrated. The embodiment of FIG. 18 is similar to that of FIG. 16, except that a plurality of discrete linearized elements 248*a*, 248*b*, and 248*c*, are carried within lumen 218 and advanced using pusher rod 232. It will be appreciated that since these linearized elements 248*a*-248*c* are separate, and unconnected, they may be released sequentially by advancing the pusher rod (and optionally retracting and/or rotating the catheter body 212) to deliver each non-linearized element. There is no need to provide for a severing mechanism as with the embodiment of FIG. 17. While three discrete linearized elements 248*a*-248*c* are illustrated, it will be appreciated that anywhere from two to 10 linearized elements, or more, could be accommodated using the approach of FIG. 18.

Figure 19E:
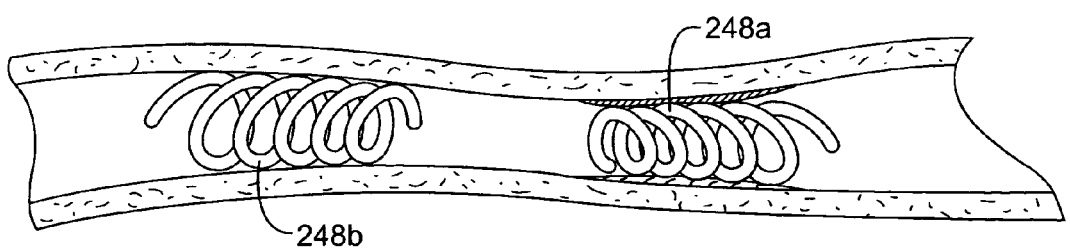
FIGS. 19A-19E illustrate use of the catheter of FIG. 15 for delivering multiple, helical prostheses at distributed points in the blood vessel.
Figure 19A:
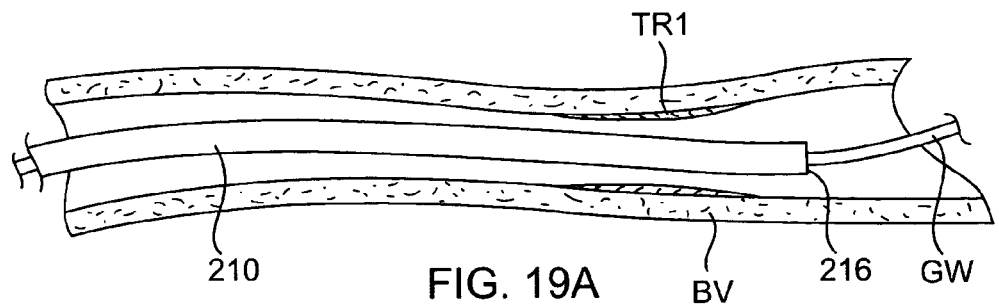
Figure 19B:
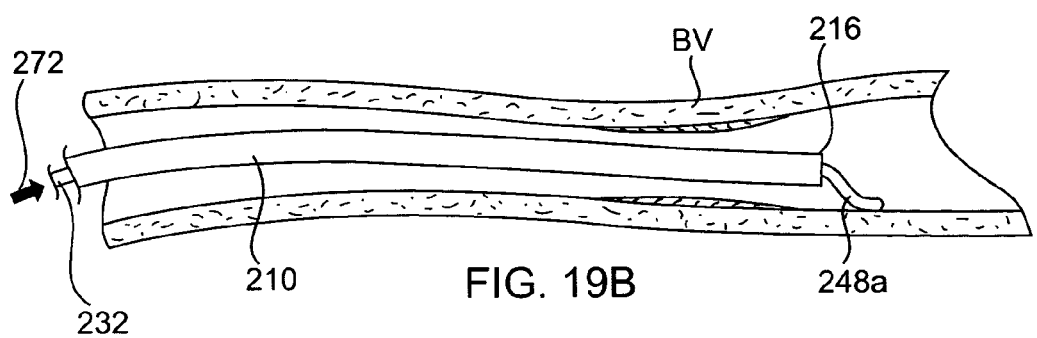
Figure 19C:
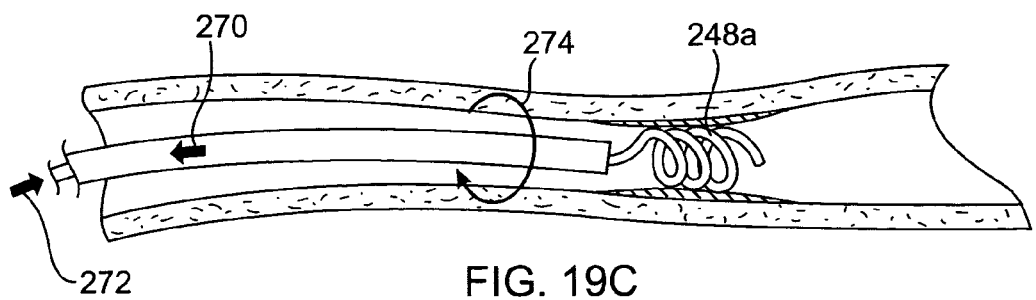

Referring now to FIGS. 19A-19C, use of the delivery catheter 10 of FIG. 15 and FIG. 17 or FIG. 18 will be illustrated. Catheter 210 is initially delivered so that its proximal end 216 lies past a first target region TR1, as shown in FIG. 19A. The catheter 210 may be introduced over a guide wire GW. The catheter may be an over-the-wire design. In some instances, however, it will be preferable to provide a rapid exchange design having a side guide wire port 260 spaced a short distance from its distal end, as shown in FIG. 16. In this way, the catheter may be introduced by withdrawing the pusher rod 232 and linearized elements approximately so that they lie behind the side guide wire port 260. The catheter may then be introduced over the conventional guide wire GW without the need to completely remove and/or exchange the pusher rod and linearized element assembly with the guide wire. Of course, for catheters having larger diameters, it would be possible to provide a separate guide wire lumen extending the entire length of the catheter for an over-the-wire introduction.

Once the catheter 210 is in place, the pusher rod 232 will be advanced so that the first non-linearized element 248 is advanced from the distal end 216, as illustrated in FIG. 19B. The pusher rod is pushed in the direction of the arrow and a leading end of the element 248*c* engages the luminal wall of the blood vessel BV.

After the element 248*c* engages the luminal wall, it is desirable to begin retracting the catheter body in the direction of arrow 270 while advancing the pusher rod 232 in the direction of arrow 272 while preferably rotating the catheter body to counteract the relative rotation of the element 248*c*. The catheter body is thus rotated in the direction of arrow 274. By appropriately controlling each of these three motions, the coil will deploy helically with minimal motion relative to the luminal wall.

Figure 19D:
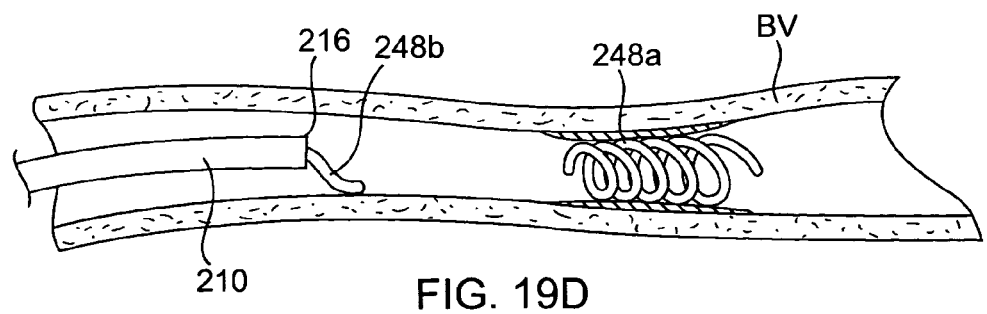

The first prostheses 248*a* will be completely delivered when it is advanced fully from the distal end 216 of catheter 210, as illustrated in FIG. 19D. The catheter 210 may continue to be withdrawn through the vasculature or other body lumen until a second region is reached where it is desired to deliver the second linearized element 248*b*. The steps of delivering the second linearized element 248*b* from the catheter are analogous to those described in FIGS. 5A-5C for the first element 248*a*. A complete deployment of the first linearized element 248*a* into its helical configuration and the second linearized element 248*b* into its helical configuration are illustrated in FIG. 19E.

It will be appreciated that the lengths, pitches, adjacent spacings, and the like, of the helical and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

Figure 20:
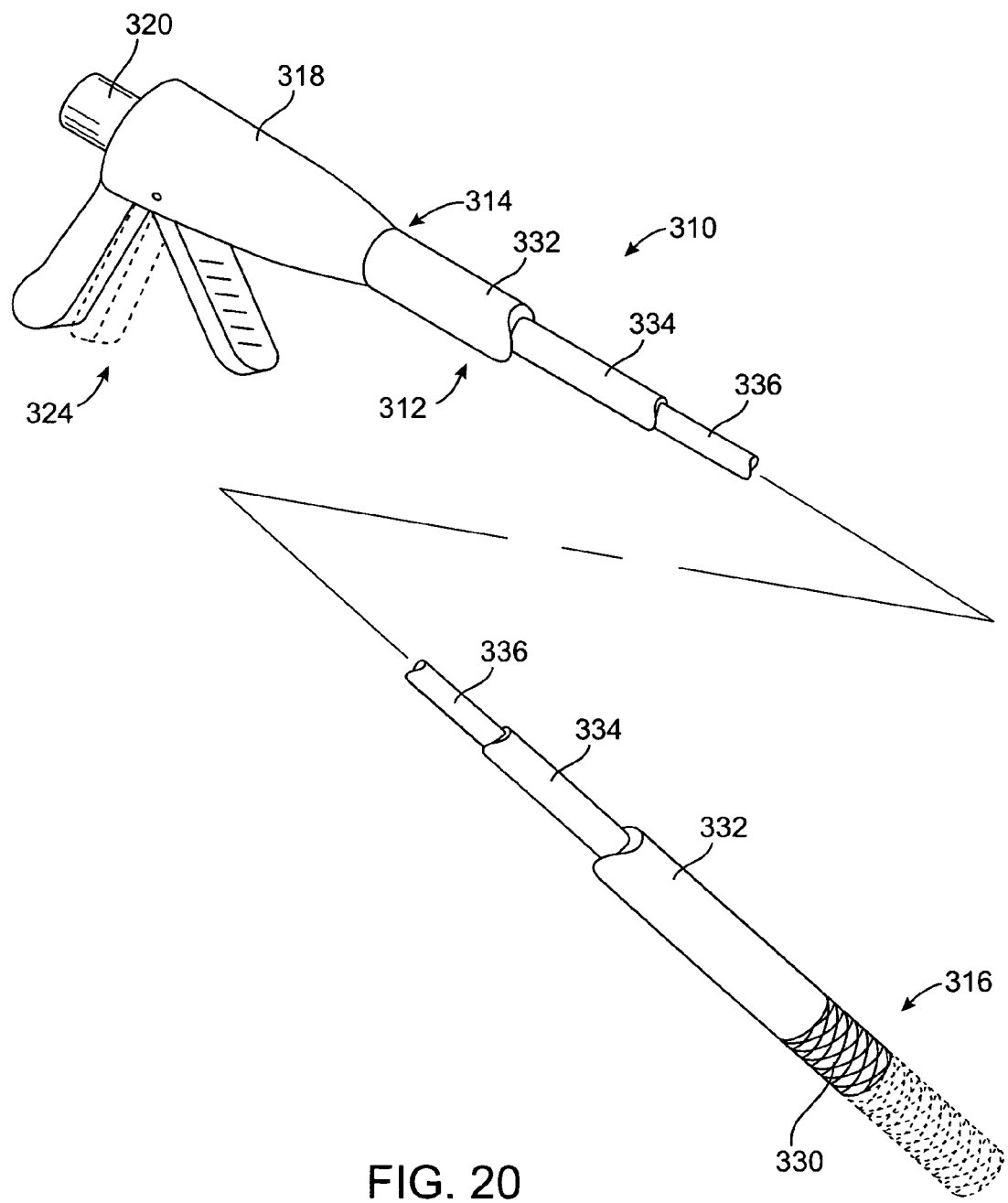
FIG. 20 is a perspective view illustrating a stent delivery catheter constructed in accordance with the principles of the present invention.

Referring now to FIG. 20, the stent delivery catheter 310 comprises a catheter body 312 having a proximal end 314 and a distal end 316. The catheter body 312 is formed from a conventional catheter material, such as a natural or synthetic polymer, such its silicone rubber. polyethylene, polyvinylchloride, polyurethane, polyester, polytetrafuoroethylene, nylon, and the like. The body may be formed as a composite having one or more reinforcement layers incorporated within a polymeric shell in order to enhance strength, flexibility, and toughness. For intravascular use, the catheter body will typically have a length in the range from 40 cm to 150 cm, usually being between 40 cm and 120 cm for peripheral blood vessels and between 110 cm and 150 cm for coronary arteries. The outer diameter of the catheter body may vary depending on the intended use, typically being between 3 French and 15 French, usually from 5 French to 9 French (one French=0.33 mm).

Catheter 310 further comprises a handle 318 at its proximal end 314. The handle has a guidewire port 320 at its distal end as well as a handle grip 324 which is actuable to extend and release evertible prosthesis 330 from the distal end 316. The catheter body 312 comprises an outer tube 332, a middle tube 334 which coaxially and slidably mounted within a lumen of the outer tube 332, and an inner tube 336 which is slidably and coaxially mounted within a lumen of the middle tube 334. Inner tube 336 has a central lumen for receiving a guidewire, as described in detail below.

Figure 21A:
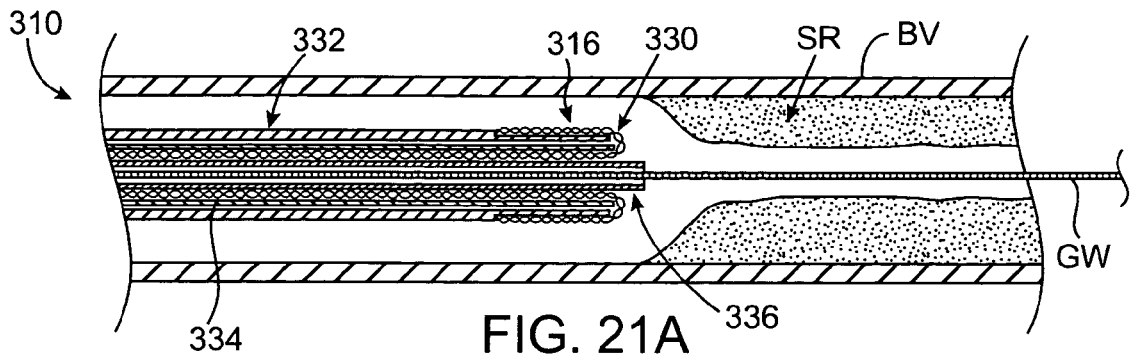
FIGS. 21A-21D illustrate use of the catheter in FIG. 20 for deploying a braided stent within a stenosed region in a blood vessel.

Referring now to FIGS. 21A-21D, delivery of the prosthesis 330 within a stenosed region SR of a blood vessel BV is described. The distal end 316 of the catheter 310 is introduced over a guidewire GW to the stenosed region SR as shown in FIG. 21A.

Figure 21B:
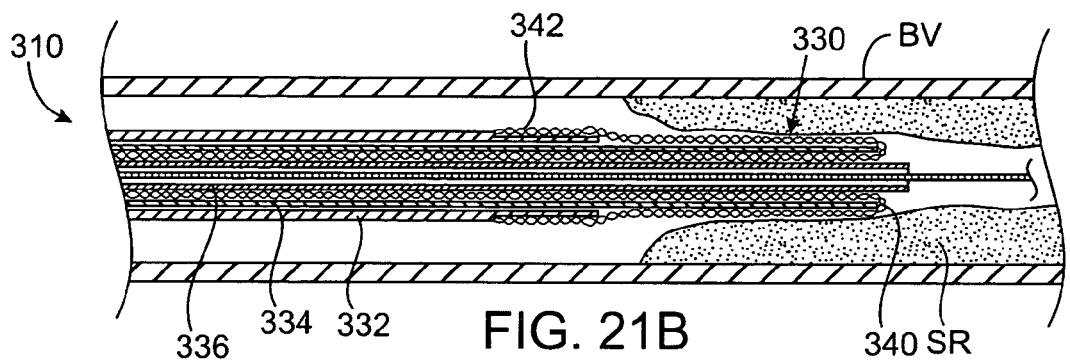

At that point, the prosthesis 330 is advanced forwardly or distally into the stenosed region SR of the blood vessel BV, as shown in FIG. 21B. In particular, both the inner tube 336 and the middle tube 334 are advanced forwardly or distally relative to the outer tube 332. This causes the leading edge 340 of the prosthesis 330 to advance into the stenosed region SR, engaging and partially dilating the lumen wall within this region.

Figure 21C:
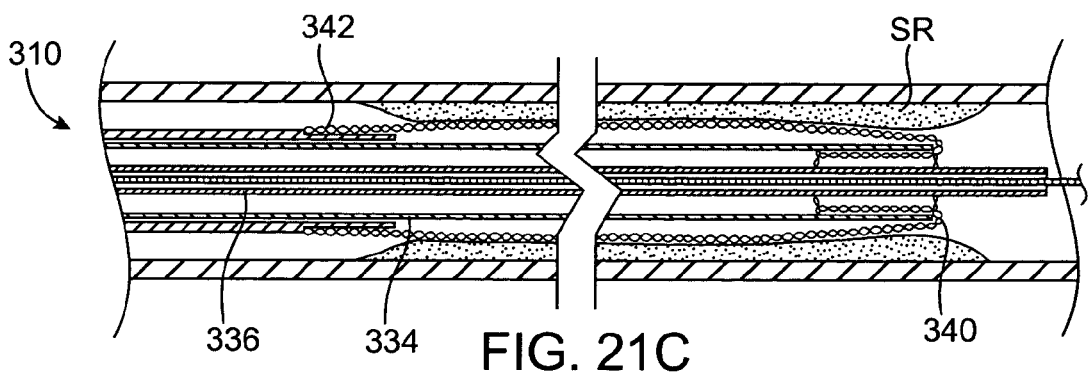

As the inner tube 336 and middle tube 334 are further advanced, as shown in FIG. 21C, the leading edge 340 of the prosthesis advances out through the other end of the stenosed region SR. During this entire deployment, fixed end 342 of the prosthesis has remained on the distal end of the outer tube 332 of the delivery catheter 310.

Figure 21D:
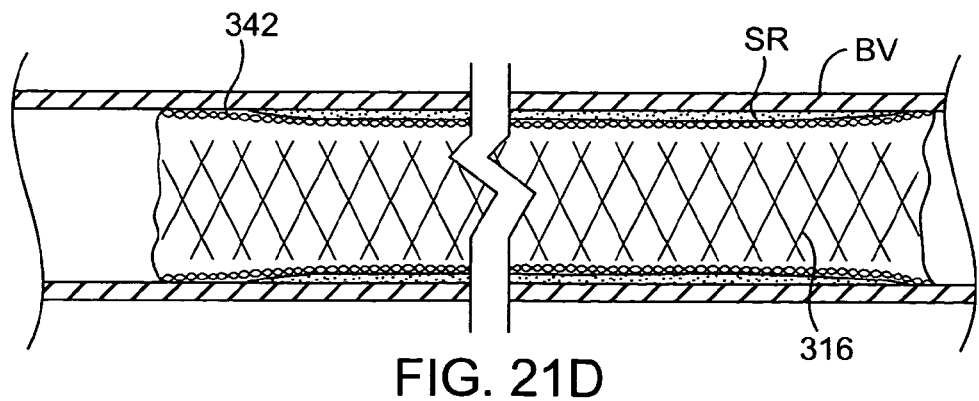

Once the prosthesis 330 is fully deployed, the outer tube 332 would be disengaged from the fixed end 342 of the prosthesis, e.g., by rotating or otherwise separating the catheter from the prosthesis, leaving the prosthesis 330 in place, as shown in FIG. 21D. As can be seen in FIG. 21D, the deployment of the prosthesis 330 has dilated the stenotic region. At this point, if the dilation is insufficient, or further anchoring of the prosthesis 330 is desired, a balloon or other expandable member may be expanded within the prosthesis 330 in a conventional manner. In one embodiment, for example, a balloon may be coupled with the outer tube 332 in such a way as to allow the balloon to be inflated to further anchor the prosthesis 330 in place.

It will be appreciated that the lengths, pitches, adjacent spacings, and the like, of the braided and other elements deployed according to the methods of the present invention can be controlled at the discretion of the treating physician. Thus, the methods and apparatus of the present invention provide useful flexibility for the treating physician to treat extended and disseminated disease in the vasculature and other body lumens.

The preferred embodiments of the invention are described above in detail for the purpose of setting forth a complete disclosure and for the sake of explanation and clarity. Those skilled in the art will envision other modifications within the scope and sprit of the present disclosure.

What is claimed is:

1. A variable length stent deployment apparatus for use in a body vessel comprising:
   a flexible catheter body having a proximal end and a distal end adapted for positioning in the vessel;
   a stenting structure releasably held by the catheter body in an unexpanded configuration, the stenting structure having a total length and being movable from the unexpanded configuration to an expanded configuration adapted to engage a wall of the vessel; and
   a deployment mechanism coupled to the catheter body adapted to apply a radially outward force along a selected length of the stenting structure to deploy a portion of the stenting structure having the selected length at one time, wherein the deployed portion having the selected length is released into the vessel in the expanded configuration while a remaining portion of the stenting structure unconnected to the deployed portion remains releasably held by the catheter body in the unexpanded configuration and wherein the deployment mechanism is coupled to an actuator at proximal end of the catheter body which allows the selected length that is expanded at one time to be varied from less than the total length up to substantially all of the total length while the catheter is positioned in the vessel.

2. The variable length stent deployment apparatus of claim 1 wherein the stenting structure comprises a plurality of stent segments, the deployment mechanism being adapted to select one or more of the stent segments, for inclusion in the deployed portion.

3. The variable length stent deployment apparatus of claim 2 wherein the deployment mechanism is adapted to deploy the plurality of stent segments simultaneously.

4. The variable length stew deployment apparatus of claim 2 further comprising a constraining element for constraining expansion of stent segments which are not to be deployed.

5. The variable length stent deployment apparatus of claim 4 wherein the constraining element is a sheath retractably disposed over stent structure and deployment mechanism.

6. The variable length stent deployment apparatus of claim 1 wherein the deployment mechanism comprises an expandable member on the catheter body, portion of the stenting structure to be deployed being positionable over the expandable member for expansion thereby.

7. The variable length stent deployment apparatus of claim 6 wherein the length of the expandable member can be selected to provide a preselected length of the deployed portion.

8. The variable length stent deployment apparatus of claim 7 wherein the length of the expandable member can be modified by a sheath slidably disposed over the expandable member for constraining expansion of a selected portion of the expandable member.

9. The variable length stent deployment apparatus of claim 6 wherein the stenting structure is movable relative to the expandable member, further comprising a stent positioner for moving a selected portion of the stenting structure relative to the expandable member.

10. The variable length stent deployment apparatus of claim 1 further comprising a valve member on the catheter body adapted to separate the portion of the stent structure to be deployed from the remaining portion.

11. The variable length stent deployment apparatus of claim 1 wherein the stenting structure has a leading end closest to the distal end of the catheter body, and the portion of the stenting structure to be deployed extends proximally a selectable length from the leading end thereof.

12. The variable length stent deployment apparatus of claim 1 further comprising a therapeutic agent on the stenting structure.

13. The variable length tent deployment apparatus of claim 12 wherein the therapeutic agent inhibits hyperplasia.

14. The variable length stent deployment apparatus of claim 12 wherein the stenting structure comprises a polymeric layer, the polymeric layer adapted to control the rate of delivery of the therapeutic agent.

15. The variable length stent deployment apparatus of claim 12 wherein the stenting comprises a bioabsorbable material.

16. A variable length stent deployment apparatus for use in a body vessel comprising:
   a flexible catheter body having a proximal end and a distal end adapted for positioning in the vessel;
   a stenting structure releasably held by the catheter body in an unexpanded configuration, the stenting structure being movable from the unexpanded configuration to an expanded configuration adapted to engage a wall of the vessel; and
   a deployment mechanism coupled to the catheter body adapted to apply a radially outward force along a selected length of the stenting structure to deploy a portion of the stenting structuring having said length, wherein the deployed portion having said length is released into the vessel in the expanded configuration while a remaining portion of the stenting structure remains releasably held by the catheter body in the unexpanded configuration, wherein the stenting structure is continuous throughout the length thereof, and the deployment mechanism is adapted to engage a selected location alone said stenting structure to separate the portion of the stenting structure to be deployed from a remaining portion of the stenting structure.

17. The variable length stent deployment apparatus of claim 16 wherein the deployment mechanism is adapted to release the deployed portion of the stenting structure distally from the distal end of the catheter body.

18. The variable length stent deployment apparatus of claim 16 wherein the stenting structure is severed by the deployment mechanism following deployment from the catheter body.

19. The variable length stent deployment apparatus of claim 16 wherein the stenting structure is a coil.

20. The variable length stent deployment apparatus of claim 16, wherein the stealing structure is a mesh.

21. The variable length stent deployment apparatus of claim 16 wherein the stenting structure comprises a plurality of stent segments, the deployment mechanism being adapted to select one or more of the stent segments for inclusion in the deployed portion.

22. The variable length stent deployment apparatus of claim 21 wherein the deployment mechanism is adapted to deploy the plurality of stent segments simultaneously.

23. The variable length stent deployment apparatus of claim 21 further comprising a constraining element for constraining expansion stent segments which are not to be deployed.

24. The variable length stent apparatus of claim 23 wherein the constraining element is a sheath retractably disposed over the stent structure and deployment mechanism.

25. The variable length stent deployment apparatus of claim 16 wherein the deployment mechanism comprises an expandable member on the catheter body, the portion of the stenting structure to be deployed being positionable over the expandable member for expansion thereby.

26. The variable length stent deployment apparatus of claim 25 wherein the length of the expandable member can be selected to provide a preselected length of the deployed portion.

27. The variable length stent deployment apparatus of claim 26 wherein the length of the expandable member can be modified by a sheath slidably disposed over the expendable member for constraining expansion of a selected portion of the expandable member.

28. The variable length stent deployment apparatus of claim 25 wherein the stenting structure is movable relative to the expendable member, further comprising a stent positioner for moving a selected portion of the stenting structure relative to the expandable member.

29. The variable length stent deployment apparatus of claim 16 further comprising a valve member on the catheter body adapted to separate the portion of the stent structure to be deployed from the remaining portion.

30. The variable length stent deployment apparatus of claim 16 wherein the stenting structure has a leading end closest to the distal end of the catheter body, and the portion of the stenting structure to be deployed extends proximally a selectable length from the leading end thereof.

31. A variable length stent deployment apparatus as in claim 16, wherein the stenting structure comprises a plurality of stent segments.

32. A variable length stent deployment apparatus as in claim 31 wherein the stent segments are linked by couplings.

33. A variable length stent deployment apparatus as in claim 32 wherein the couplings are separable.

34. A variable length stent deployment apparatus as in claim 31 wherein the couplings are frangible.

35. A variable length stent deployment apparatus as in claim 31 wherein the couplings are bioerodable.

36. The variable length stent deployment apparatus of claim 16 further comprising a therapeutic agent.

37. The variable length stent deployment apparatus of claim 36 wherein the therapeutic agent inhibits hyperplasia.

38. The variable length stent deployment apparatus of claim 36 wherein the stenting structure comprises a polymeric layer, the polymeric layer adapted to control the rate of delivery of the therapeutic agent.

39. The variable length stent deployment apparatus of claim 36 wherein the stenting structure comprises a bioabsorbable material.

40. A method of deploying a stent of selectable length in a vessel, the method comprising;
endovascularly positioning a catheter in the vessel, the catheter having a distal end and stenting structure releasably disposed therein, the stenting structure having a total length;
uncovering a portion of the stenting structure prior to deployment from the catheter;
determining a desired stent length;
while the catheter remains positioned in the vessel, adjusting the length of the uncovered portion to be at least equal to the desired stent length; and
applying a radially outward force to the stenting structure to expand only the uncovered portion, wherein the uncovered portion expands at one time to engage a wall of the vessel and separates from any remaining portion of the stenting structure which remains covered in the catheter, and wherein the length of the uncovered portion which expands at one time may be varied from less than the total length up to substantially all of the total length while the catheter is positioned in the vessel.

41. The method of claim 40 wherein adjusting the length of the uncovered portion comprises positioning a first portion of the stenting structure shorter than the desired stent length in a position in the catheter for deployment, and positioning an additional portion of the stenting structure in the catheter adjacent to the first portion for deployment therewith.

42. The method of claim 40 wherein adjusting the length of the uncovered portion comprises axially moving the deployable portion relative to the remaining portion.

43. The method of claim 40 further comprising:
determining a second stent length different than the desired stent length;
selecting a second portion of the stenting structure having the second stent length; and
releasing the second portion in the vessel, wherein the second portion expands to engage a wall of the vessel.

44. The method of claim 40 wherein applying the radially outward force comprises expanding an expandable member, further comprising adjusting the length of the expandable member to be at least as long as the uncovered portion of the stent.

45. The method of claim 40, wherein the stenting structure comprises a plurality of stent segments and adjusting the length of the uncovered portion comprises repositioning a first stent segment relative to a second stent segment.

46. The method of claim 45 wherein the stent segments are connected by separable couplings.

47. The method of claim 45 wherein the stent segments are unconnected to each other.

48. The method of claim 40 wherein the covered stent segment is constrained by a sheath disposed over the covered stent segment.

49. The method of claim 40 wherein adjusting the length of the uncovered portion comprises engaging a valve member against the stenting structure to separate the uncovered portion from the covered portion of the stenting structure.

50. The method of claim 40 wherein the stenting structure has a leading end closest to the distal end of the catheter, and wherein adjusting the length of the uncovered portion comprises selecting a desired length of the stenting structure extending proximally from the leading end thereof.

51. The method of claim 40 wherein the stenting structure is continuously connected through the length thereof, and adjusting the length of the uncovered portion comprises separating the deployable portion of the stenting structure from a covered portion of the tenting structure at a selectable location on the stenting structure.

52. The method of claim 51 wherein adjusting the length of the uncovered portion comprises severing the stenting structure at the selectable location.

53. The method of claim 51 wherein the uncovered portion is separated following deployment by the deployment mechanism.

54. The method of claim 51 wherein the stenting structure is a coil.

55. The method of claim 51 wherein the stenting structure is a mesh.

56. The method of claim 40 wherein adjusting the length of the uncovered portion comprises advancing the desired length of the stent structure distally of the catheter.

57. The method of claim 40 further comprising:
repositioning the catheter in the vessel;
determining a second stent length;
selecting a second portion of the stenting structure having the second length; and
releasing the second portion in the vessel, wherein the second portion expands to engage a wall of the vessel.

58. The method of claim 40 further comprising releasing a therapeutic agent from the stenting structure after releasing the stenting structure in the vessel.

59. The method of claim 58 wherein the therapeutic agent inhibits hyperplasia.

60. The method of claim 58 wherein the stenting structure comprises a polymeric layer, the polymeric layer adapted to control the rate of delivery of the therapeutic agent.

61. The method of claim 58 wherein the stenting structure comprises a bioabsorable material.

62. The method of claim 40 wherein uncovering a portion of the stenting structure comprises retracting a sheath.

63. The method of claim 40 wherein uncovering a portion of the stenting structure comprises advancing a pusher member.

64. The method of claim 40 wherein applying a radially outward force comprises inflating a balloon.

65. The method of claim 40 further comprising severing the uncovered portion from any remaining portion of the stenting structure which remains covered in the catheter.

66. A method of deploying a stent of selectable length in a vessel, the method comprising:
endovascularly positioning a catheter in the vessel, the catheter having a distal end and a stenting structure releasably disposed therein;
uncovering a portion of the stenting structure prior to deployment from the catheter;
determining a desired stent length;
adjusting the length of the uncovered portion to be at least equal to the desired stent length; and
applying a radially outward force to the stent structure to expand only the uncovered portion from the catheter into the vessel, wherein the uncovered portion expands to engage a wall of the vessel while a remaining portion of the stenting structure remains covered in the catheter, wherein adjusting the length of the uncovered portion comprises engaging a valve member against the stenting structure to separate the uncovered portion from the covered portion of the stenting structure, and wherein a sheath is slidably disposed over the stenting structure, the valve member being disposed at a distal end of the sheath.

67. The method of claim 43 wherein the uncovered portion and the second portion are deployed from a fixed position relative to the distal end of the catheter.

68. The method of claim 66 further comprising:
repositioning the catheter in the vessel;
determining a second stent length;
selecting a second portion of the stenting structure having the second length; and
releasing the second portion in the vessel, wherein the second portion expands to engage a wall of the vessel.

69. The method of claim 68 wherein the uncovered portion and the second portion are deployed from a fixed position relative to the distal end of the catheter.

70. The method of claim 66 further comprising releasing a therapeutic agent from the stenting structure after releasing the stenting structure in the vessel.

71. The method of claim 70 wherein the therapeutic agent inhibits hyperplasia.

72. The method of claim 70 wherein the stenting structure comprises a polymeric layer, the polymeric layer adapted to control the rate of delivery of the therapeutic agent.

73. The method of claim 70 wherein the stenting structure comprises a bioabsorable material.

74. The method of claim 66, wherein adjusting the length of the uncovered portion comprises positioning a first portion of the stenting structure shorter than the desired stent length in a position in the catheter for deployment, and positioning an additional portion of the stenting structure in the catheter adjacent to the first portion for deployment therewith.

75. The method of claim 66 wherein uncovering a portion of the stenting structure comprises retracting a sheath.

76. The method of claim 66 wherein uncovering a portion of the stenting structure comprises axially moving a sheath relative to a pusher member.

77. The method of claim 66 wherein applying a radially outward force comprises inflating a balloon.

78. The method of claim 66 further comprising, severing the uncovered portion from any remaining portion of the stenting structure which remains covered in the catheter.

79. The method of claim 66 wherein adjusting the length of the uncovered portion comprises axially moving the deployable portion relative to the remaining portion.

80. The method of claim 66 wherein applying the radially outward force comprises expanding an expandable member, further comprising adjusting the length of the expandable member to be at least as long as the uncovered portion of the stent.

81. The method of claim 66 wherein the stenting structure comprises a plurality of stent segments and adjusting the length of the uncovered portion comprises repositioning a first stent segment relative to a second stent segment.

82. The method of claim 81 wherein the stent segments are connected by separable couplings.

83. The method of claim 81 wherein the intent segments are unconnected to each other.

84. The method of claim 66 wherein the covered stent segment is constrained by a sheath disposed over the covered stent segment.

85. The method of claim 66 wherein the stenting structure has a leading end closest to the distal end of the catheter, and wherein adjusting the length of the uncovered portion comprises selecting a desired length of the stenting structure extending proximally from the leading end thereof.

86. The method of claim 66 wherein the stenting structure is continuously connected through the length thereof, and adjusting the length of the uncovered portion comprises separating the deployable portion of the stenting structure from a covered portion of the stating structure at a selectable location on the stenting structure.

87. The method of claim 86 wherein adjusting the length of the uncovered portion comprises severing the stenting structure at the selectable location.

88. The method of claim 66 wherein adjusting the length of the uncovered portion comprises advancing the desired length of the stent structure distally of the catheter.

89. The method of claim 86 wherein the uncovered portion is separated following deployment by the deployment mechanism.

90. The method of claim 86 wherein the stenting structure is a coil.

91. The method of claim 86 wherein the stenting structure is a mesh.

* * * * *